United States Patent
McGarry et al.

(10) Patent No.: US 7,576,109 B2
(45) Date of Patent: Aug. 18, 2009

(54) 1,3,4-OXADIAZOL-2-ONES AS PPAR DELTA MODULATORS AND THEIR USE THEREOF

(75) Inventors: Daniel G. McGarry, Branchburg, NJ (US); Karen Chandross, Somerset, NJ (US); Jean Merrill, Whippany, NJ (US); Jochen Goerlitzer, Frankfurt am Main (DE); Stefanie Keil, Hofheim (DE); Wolfgang Wendler, Selters (DE); Patrick Bernardelli, Villepreux (FR)

(73) Assignees: Aventis Pharmaceuticals Inc., Bridgewater, NJ (US); Sanofi-Aventis Deutschland GmbH, Frankfurt am Main (DE)

( * ) Notice: Subject to any disclaimer, the term of this patent is extended or adjusted under 35 U.S.C. 154(b) by 319 days.

(21) Appl. No.: 11/535,227

(22) Filed: Sep. 26, 2006

(65) Prior Publication Data

US 2007/0060626 A1 Mar. 15, 2007

Related U.S. Application Data

(63) Continuation of application No. PCT/US2005/010854, filed on Mar. 30, 2005.

(60) Provisional application No. 60/558,419, filed on Apr. 1, 2004.

(51) Int. Cl.
*A61K 31/4245* (2006.01)
*C07D 271/10* (2006.01)
*C07D 413/10* (2006.01)

(52) U.S. Cl. ............... 514/364; 548/125; 548/143; 548/144; 514/361

(58) Field of Classification Search ............... 548/125, 548/143, 144; 514/361, 364
See application file for complete search history.

(56) References Cited

U.S. PATENT DOCUMENTS

| 4,895,953 | A | * | 1/1990 | Musser et al. ........... 548/204 |
| 5,103,014 | A | * | 4/1992 | Musser et al. ........... 548/204 |
| 5,641,796 | A | * | 6/1997 | Dominianni et al. ..... 514/374 |
| 7,208,509 | B2 | * | 4/2007 | Dunn et al. ............. 514/363 |

FOREIGN PATENT DOCUMENTS

| WO | WO 00/78313 | 12/2000 |
| WO | WO 01/00603 | 1/2001 |
| WO | WO 01/17994 | 3/2001 |

OTHER PUBLICATIONS

Henke, B.R.,, N-(2-Benzolphenyl)-L-Tyrosine PPAR-Gamma Agonists. 1. Discovery of a Novel Series of Potent Antihyperglycemic and Antihyperlipidemic Agents, J. Med. Chem. (1998) vol. 41, pp. 5020-5036.

Kulkarni, S.S., et. al., Three-Dimensional Quantilative Structure Activity Relationships (3-D-QSAR) of Antihyperglycemic Agents, Bioorganic & Medicinal Chemistry vol. 7, (1999) pp. 1475-1485.

* cited by examiner

*Primary Examiner*—Golam M Shameem
(74) *Attorney, Agent, or Firm*—Jiang Lin; Craig M. Bell

(57) ABSTRACT

The present invention is directed to 1,3,4-oxadiazolones, compounds of formula I and their pharmaceutically acceptable salts stereoisomers, tautomers, or solvates thereof. Novel compounds include those of formula I, in which radicals are as defined herein.

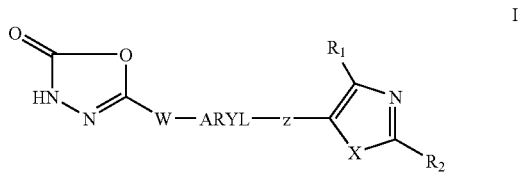

The compounds of this invention are modulators of PPAR-delta and therefore useful as pharmaceutical agents, especially for the treatment of demyelinating diseases and disorders of fatty acid metabolism and glucose utilization.

15 Claims, No Drawings

1,3,4-OXADIAZOL-2-ONES AS PPAR DELTA MODULATORS AND THEIR USE THEREOF

CROSS-REFERENCE TO RELATED APPLICATIONS

This application is a continuation of International Application No. PCT/US2005/010854 filed on Mar. 30, 2005 which is incorporated herein by reference in its' entirety which also claims the benefit of priority of U.S. Provisional Appln. No 60/558,419 filed on Apr. 1, 2004.

FIELD OF THE INVENTION

This invention relates to novel compounds and pharmaceutical formulations that act as selective PPARdelta ligand receptor binders, which are useful in modulating PPARdelta receptors for the treatment of diseases mediated by nuclear hormone receptors. The PPARdelta ligand receptor binders of this invention are useful as agonists or antagonists of the PPARdelta receptor.

BACKGROUND OF THE INVENTION

The peroxisome proliferator-activated receptors (PPARs) comprise a subfamily of the nuclear receptor superfamily. Four closely related isoforms have been identified and cloned and are commonly known as PPARalpha, PPARgamma-1, PPARgamma-2 and PPARdelta. Each receptor subtype has a signature DNA binding domain (DBD) and a ligand-binding domain (LBD), both being necessary for ligand activated gene expression. PPARs bind as heterodimers with a retinoid X receptor. See J. Berger and D. E. Miller, *Annu. Rev. Med.,* 2002, 53, 409-435.

PPARdelta (also known as PPARbeta) is expressed in a broad range of mammalian tissue, but little information regarding its biological functions or the full array of genes regulated by the receptor has been elucidated. However, it has recently been found that agonists may be useful to treat conditions such as dyslipidemia and certain dermatological conditions, while antagonists may be useful in the treatment of a wide variety of conditions such as osteoporosis or colorectal cancer (D. Sternbach, in *Annual Reports in Medicinal Chemistry, Volume* 38, A. M. Doherty, ed., Elsevier Academic Press, 2003 pp. 71-80).

PPARdelta appears to be significantly expressed in the CNS; however much of its function there still remains undetermined. Of singular interest however, is the discovery that PPARdelta was expressed in rodent oligodendrocytes, the major lipid-producing cells of the CNS (J. Granneman, et al., *J. Neurosci. Res.,* 1998, 51, 563-573). Moreover, it was also found that a PPARdelta selective agonist was found to significantly increase oligodendroglial myelin gene expression and myelin sheath diameter in mouse cultures (I. Saluja et al., *Glia,* 2001, 33, 194-204). Thus, PPARdelta activators may be useful in the treatment of both demyelinating and dysmyelinating diseases.

Demyelinating conditions are manifested in loss of myelin—the multiple dense layers of lipids and protein which cover many nerve fibers. These layers are provided by oligodendroglia in the central nervous system (CNS), and Schwann cells in the peripheral nervous system (PNS). In patients with demyelinating conditions, demyelination may be irreversible; it is usually accompanied or followed by axonal degeneration, and often by cellular degeneration. Demyelination can occur as a result of neuronal damage or damage to the myelin itself—whether due to aberrant immune responses, local injury, ischemia, metabolic disorders, toxic agents, or viral infections (Prineas and McDonald, *Demyelinating Diseases. In Greenfield's Neuropathology,* 6.sup.th ed. (Edward Arnold: New York, 1997) 813-811; Beers and Berkow, eds., *The Merck Manual of Diagnosis and Therapy,* 17.sup.th ed. (Whitehouse Station, N.J.: Merck Research Laboratories, 1999) 1299, 1437, 1473-76, 1483).

Central demyelination (demyelination of the CNS) occurs in several conditions, often of uncertain etiology, that have come to be known as the primary demyelinating diseases. Of these, multiple sclerosis (MS) is the most prevalent. Other primary demyelinating diseases include adrenoleukodystrophy (ALD), adrenomyeloneuropathy, AIDS-vacuolar myelopathy, HTLV-associated myelopathy, Leber's hereditary optic atrophy, progressive multifocal leukoencephalopathy (PML), subacute sclerosing panencephalitis, Guillian-Barre syndrome and tropical spastic paraparesis. In addition, there are acute conditions in which demyelination can occur in the CNS, e.g., acute disseminated encephalomyelitis (ADEM) and acute viral encephalitis. Furthermore, acute transverse myelitis, a syndrome in which an acute spinal cord transection of unknown cause affects both gray and white matter in one or more adjacent thoracic segments, can also result in demyelination. Also, disorders in which myelin-forming glial cells are damaged including spinal cord injuries, neuropathies and nerve injury often result in demyeliation.

Selective PPARdelta modulators may also be useful for treating or preventing other disease states see, for example, Joel Berger et al., Annu. Rev. Med. 2002, 53, 409-435; Timothy Wilson et al. J. Med. Chem., 2000, Vol. 43, No. 4, 527-550; Steven Kliewer et al., Recent Prog Horm Res. 2001; 56: 239-63; Jean-Charles Fruchart, Bart Staels and Patrick Duriez: PPARS, Metabolic Disease and Arteriosclerosis, Pharmacological Research, Vol. 44, No. 5, 345-52; 2001; Sander Kersten, Beatrice Desvergne & Walter Wahli: Roles of PPARs in Health and Disease, Nature, vol 405, 25 May 2000; 421-4; Ines Pineda Torra, Giulia Chinetti, Caroline Duval, Jean-Charles Fruchart and Bart Staels: Peroxisome Proliferator-Activated Receptors: From Transcriptional Control to Clinical Practice, Curr Opin Lipidol 12: 2001, 245-254).

Compounds acting as PPARdelta modulators may be particularly suitable for the treatment and/or prevention of disorders of fatty acid metabolism and glucose utilization disorders in which insulin resistance is involved such as diabetes mellitus, especially type-2 diabetes, including the prevention of dyslipidemia and the sequelae associated therewith. Particular conditions resulting therefrom include hyperglycemia, improvement in insulin resistance, improvement in glucose tolerance, protection of the pancreatic β cells as well as the prevention of macro- and microvascular disorders.

Dyslipidemias and their sequelae such as, for example, atherosclerosis, coronary heart disease, cerebrovascular disorders etc, especially those (but not restricted thereto) which are characterized by one or more of the following factors: high plasma triglyceride concentrations, high postprandial plasma triglyceride concentrations, low HDL cholesterol concentrations, low ApoA lipoprotein concentrations, high LDL cholesterol concentrations, low density LDL cholesterol particles, high ApoB lipoprotein concentrations.

Various other conditions which may be associated with the metabolic syndrome, such as: obesity (excess weight), including central obesity, thromboses, hypercoagulable and prothrombotic states (arterial and venous), high blood pressure, heart failure such as, for example (but not restricted thereto), following myocardial infarction, hypertensive heart disease or cardiomyopathy.

Other disorders or conditions in which inflammatory reactions or cell differentiation, may, for example, be involved are: atherosclerosis such as, for example (but not restricted thereto), coronary sclerosis including angina pectoris or myocardial infarction, stroke, vascular restenosis or reocclusion, chronic inflammatory bowel diseases, such as, for example, Crohn's disease and ulcerative colitis, pancreatitis, other inflammatory states, retinopathy, adipose cell tumors, lipomatous carcinomas such as, for example, liposarcomas, solid tumors and neoplasms such as, for example (but not restricted thereto), carcinomas of the gastrointestinal tract, of the liver, of the biliary tract and of the pancreas, endocrine tumors, carcinomas of the lungs, of the kidneys and the urinary tract, of the genital tract, prostate carcinomas etc., acute and chronic myeloproliferative disorders and lymphomas angiogenesis, neurodegenerative disorders, Alzheimer's disease, Parkinson's disease, erythemato-squamous dermatoses such as, for example, psoriasis, acne vulgaris.

Other skin disorders and dermatological conditions modulated by PPARdelta:

eczemas and neurodermitis, dermatitis such as, for example, seborrheic dermatitis or photodermatitis, keratitis and keratoses such as, for example, seborrheic keratoses, senile keratoses, actinic keratosis, photo-induced keratoses or keratosis follicularis, keloids and keloid prophylaxis, warts, including condylomata or condylomata acuminata, human papilloma viral (HPV) infections such as, for example, venereal papillomata, viral warts such as, for example, molluscum contagiosum, leukoplakiapapular dermatoses such as, for example, Lichen planus, skin cancer such as, for example, basal-cell carcinomas, melanomas or cutaneous T-cell lymphomas, localized benign epidermal tumors such as, for example, keratoderma, epidermal naevi and chilblains.

Various other conditions potentially modulated by PPARdelta including syndrome X, polycystic ovary syndrome (PCOS), asthma osteoarthritis, lupus erythematosus (LE) or inflammatory rheumatic disorders such as, for example, rheumatoid arthritis, vasculitis, wasting (cachexia), gout ischemia/reperfusion syndrome and acute respiratory distress syndrome (ARDS).

SUMMARY OF THE INVENTION

The present invention is directed to compound of formula I.

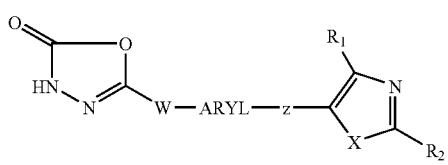

wherein
ARYL is phenyl or pyridinyl, wherein said phenyl or pyridinyl is optionally substituted with one or more substituents selected from the group consisting of halogen, $C_{1-6}$alkyl, $C_{2-6}$alkenyl, $C_{1-6}$-alkoxy, $C_{1-6}$perfluoroalkyl; $C_{1-6}$alkylthio, hydroxy, hydroxy$C_{1-6}$alkyl, $C_{1-4}$acyloxy, nitro, cyano, $C_{1-6}$alkylsulfonyl, amino, $C_{1-6}$alkylamino and $C_{1-6}$alkoxycarbonyl;

W is a bond or $(CH_2)_m$, wherein m is an integer from 1 to 4;
Z is —O$(CH_2)_n$—, —SO$_2$$(CH_2)_n$—, —$(CH_2)_n$—Y—$(CH_2)_n$—, —$(CH_2)_n$—CO—, —O$(CH_2)_n$—CO— or —$(CH_2)_n$—Y—$(CH_2)_n$—CO— wherein Y is NR$_3$, O or S and R$_3$ is selected from the group consisting of H, $C_{1-6}$alkyl, $C_{3-8}$cycloalkyl, $C_{1-6}$alkyl$C_{3-8}$cycloalkyl and benzyl and n is independently an integer from 1 to 5;
X is NR$_3$, O or S wherein R$_3$ is as defined above;
R$_1$ is H, halogen, $C_{1-6}$alkyl, $C_{1-6}$alkoxy, $C_{1-6}$perfluoroalkyl; hydroxy$C_{1-6}$alkyl, nitro, cyano, and $C_{1-6}$alkylamino; and
R$_2$ is substituted or unsubstituted phenyl, pyridinyl or thienyl wherein the substituents are selected from the group consisting of halogen, $C_{1-6}$alkyl, $C_{2-6}$alkenyl, $C_{1-6}$alkoxy, $C_{1-6}$perfluoroalkyl, $C_{1-6}$alkylthio, hydroxy, hydroxy$C_{1-6}$alkyl, $C_{1-4}$acyloxy, nitro, cyano, $C_{1-6}$alkylsulfonyl, amino, $C_{1-6}$alkylamino and $C_{1-6}$alkoxycarbonyl; or a stereoisomer, a tautomer or a solvate thereof or a pharmaceutically acceptable salt thereof.

The present invention is also directed to pharmaceutical compositions of formula I, and methods of using said compounds and compositions for modulating PPARdelta in a subject in need of such modulation by administering a compound which preferentially modulates the activity of PPARdelta. The present compounds possess useful PPARdelta modulating activity, and are expected to be useful in the treatment or prophylaxis of a disease or condition in which said disease is capable of being treated by modulation of PPARdelta ligand binding activity, by administering to the patient a therapeutically effective amount of the compound of formula I.

DETAILED DESCRIPTION OF THE INVENTION

The terms as used herein have the following meanings:
As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl and tert-butyl. Derived expressions such as "$C_{1-6}$alkoxy", "$C_{1-6}$alkoxy$C_{1-6}$alkyl", "hydroxy$C_{1-6}$alkyl", "$C_{1-6}$alkylcarbonyl", "$C_{1-6}$alkoxycarbonyl$C_{1-6}$alkyl", "$C_{1-6}$alkoxycarbonyl", "amino$C_{1-6}$alkyl", "$C_{1-6}$alkylcarbamoyl$C_{1-6}$alkyl", "$C_{1-6}$dialkylcarbamoyl$C_{1-6}$alkyl" "mono- or di-$C_{1-6}$alkylamino$C_{1-6}$alkyl", amino$C_{1-6}$alkylcarbonyl", "diphenyl$C_{1-6}$alkyl", "aryl$C_{1-6}$alkyl", "arylcarbonyl$C_{1-6}$alkyl" and "aryloxy$C_{1-6}$alkyl" are to be construed accordingly.

As used herein, the expression "$C_{2-6}$alkenyl" includes ethenyl and straight-chained or branched propenyl, butenyl, pentenyl and hexenyl groups. Similarly, the expression "$C_{2-6}$alkynyl" includes ethynyl and propynyl, and straight-chained or branched butynyl, pentynyl and hexynyl groups.

As used herein "aryl" represents a carbocyclic aromatic ring system such as phenyl, biphenyl, naphthyl, anthracenyl, phenanthrenyl, fluorenyl, indenyl, pentalenyl, azulenyl, biphenylenyl and the like. Aryl is also intended to include the partially hydrogenated derivatives of the carbocyclic aromatic systems enumerated above. Non-limiting examples of such partially hydrogenated derivatives are 1,2,3,4-tetrahydronaphthyl, 1,4-dihydronaphthyl and the like.

As used herein "aryloxy" represents a group —O-aryl wherein aryl is as defined above.

As used herein "heteroaryl" (on its own or in any combination, such as "heteroaryloxy", or "heteroaryl alkyl")—a 5-10 membered aromatic ring system in which one or more rings contain one or more heteroatoms selected from the group consisting of N, O or S, such as, but not limited, to pyrrole, pyrazole, furan, thiophene, quinoline, isoquinoline, quinazolinyl, pyridine, pyrimidine, oxazole, thiazole, thiadiazole, tetrazole, triazole, imidazole, or benzimidazole.

As used herein "heterocyclic or heterocyclyl" (on its own or in any combination, such as "heterocyclylalkyl")—a saturated or partially unsaturated 4-10 membered ring system in which one or more rings contain one or more heteroatoms selected from the group consisting of N, O, or S; such as, but not limited to, pyrrolidine, piperidine, piperazine, morpholine, tetrahydro pyran, or imidazolidine.

As used herein, the expression "$C_{1-6}$ perfluoroalkyl" means that all of the hydrogen atoms in said alkyl group are replaced with fluorine atoms. Illustrative examples include trifluoromethyl and pentafluoroethyl, and straight-chained or branched heptafluoropropyl, nonafluorobutyl, undecafluoropentyl and tridecafluorohexyl groups. Derived expression, "$C_{1-6}$ perfluoroalkoxy", is to be construed accordingly.

As used herein, the expression "$C_{3-8}$cycloalkyl" means cyclopropyl, cyclobutyl, cyclopentyl, cyclohexyl, cycloheptyl and cyclooctyl.

As used herein, the expression "$C_{3-8}$cycloalkyl$C_{1-6}$alkyl" means that the $C_{3-8}$cycloalkyl as defined herein is further attached to $C_{1-6}$alkyl as defined herein. Representative examples include cyclopropylmethyl, 1-cyclobutylethyl, 2-cyclopentylpropyl, cyclohexylmethyl, 2-cycloheptylethyl and 2-cyclooctylbutyl and the like.

As used herein "halogen" or "halo" means chloro, fluoro, bromo, and iodo.

As used herein "$C_{1-6}$alkylsulfonyl" in the present context designates a group —S(=O)$_2$C$_{1-6}$alkyl wherein C$_{1-6}$alkyl is as defined above. Representative examples include, but are not limited to, methylsulfonyl, ethylsulfonyl, n-propylsulfonyl, isopropylsulfonyl, butylsulfonyl, iso-butylsulfonyl, sec-butylsulfonyl, tert-butylsulfonyl, n-pentylsulfonyl, isopentylsulfonyl, neopentylsulfonyl, tert-pentylsulfonyl, n-hexylsulfonyl, isohexylsulfonyl and the like.

As used herein "arylsulfonyl" represents a group —S(=O)$_2$aryl wherein aryl is as defined above.

As used herein "heteroarylsulfonyl" represents a group —S(=O)$_2$heteroaryl wherein heteroaryl is as defined above.

The expression "stereoisomers" is a general term used for all isomers of the individual molecules that differ only in the orientation of their atoms in space. Typically it includes mirror image isomers that are usually formed due to at least one asymmetric center, (enantiomers). Where the compounds according to the invention possess two or more asymmetric centers, they may additionally exist as diastereoisomers, also certain individual molecules may exist as geometric isomers (cis/trans). It is to be understood that all such isomers and mixtures thereof in any proportion are encompassed within the scope of the present invention.

"Substituted" means substituted by 1 to 2 substituents independently selected from the group consisting of $C_{1-6}$ alkyl, $C_{1-6}$ perfluoroalkyl, hydroxy, —CO$_2$H, an ester, an amide, $C_1$-$C_6$ alkoxy, $C_1$-$C_6$ perfluoroalkoxy, —NH$_2$, Cl, Br, I, F, —NH-lower alkyl, and —N(lower alkyl)$_2$.

The compounds and salts of the present invention may exist in several tautomeric forms, including the enol and imine form, and the keto and enamine form and geometric isomers and mixtures thereof. All such tautomeric forms are included within the scope of the present invention. Tautomers exist as mixtures of a tautomeric set in solution. In solid form, usually one tautomer predominates. Even though one tautomer may be described, the present invention includes all tautomers of the present compounds.

As used herein the term "modulator" refers to a chemical compound with capacity to either enhance (e.g., "agonist" activity) or inhibit (e.g., "antagonist" activity) a functional property of biological activity or process (e.g., enzyme activity or receptor binding); such enhancement or inhibition may be contingent on the occurrence of a specific event, such as activation or repression of a signal transduction pathway and/or may be manifest only in particular cell types and may result in a measurable biological change.

As used herein, "patient" means a warm blooded animal, such as for example rat, mice, dogs, cats, guinea pigs, and primates such as humans.

As used herein, the expression "pharmaceutically acceptable carrier" means a non-toxic solvent, dispersant, excipient, adjuvant, or other material which is mixed with the compound of the present invention in order to permit the formation of a pharmaceutical composition, i.e., a dosage form capable of administration to the patient. One example of such a carrier is a pharmaceutically acceptable oil typically used for parenteral administration.

The term "pharmaceutically acceptable salts" as used herein means that the salts of the compounds of the present invention can be used in medicinal preparations. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, hydrobromic acid, sulfuric acid, methanesulfonic acid, 2-hydroxyethanesulfonic acid, p-toluenesulfonic acid, fumaric acid, maleic acid, hydroxymaleic acid, malic acid, ascorbic acid, succinic acid, glutaric acid, acetic acid, salicylic acid, cinnamic acid, 2-phenoxybenzoic acid, hydroxybenzoic acid, phenylacetic acid, benzoic acid, oxalic acid, citric acid, tartaric acid, glycolic acid, lactic acid, pyruvic acid, malonic acid, carbonic acid or phosphoric acid. The acid metal salts such as sodium monohydrogen orthophosphate and potassium hydrogen sulfate can also be formed. Also, the salts so formed may present either as mono- or di-acid salts and can exist either as hydrated or can be substantially anhydrous. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "therapeutically effective amount" as used herein means an amount of the compound which is effective in treating the named disorder or condition.

The invention also provides pharmaceutical compositions comprising one or more of the compounds according to this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. An erodible polymer containing the active ingredient may be envisaged. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Flavored unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

In the treatment of various disease states as described herein, a suitable dosage level is about 0.01 to 250 mg/kg per day, preferably about 0.05 to 100 mg/kg per day, and especially about 0.05 to 20 mg/kg per day. The compounds may be administered on a regimen of 1 to 4 times per day.

As used in the examples and preparations that follow, the terms used therein shall have the meanings indicated: "kg" refers to kilograms, "g" refers to grams, "mg" refers to milligrams, "µg" refers to micrograms, "pg" refers to picograms, "mol" refers to moles, "mmol" refers to millimoles, "nmole" refers to nanomoles, "L" refers to liters, "mL" or "ml" refers to milliliters, "µL" refers to microliters, "° C." refers to degrees Celsius, "$R_f$" refers to retention factor, "mp" or "m.p." refers to melting point, "dec" refers to decomposition, "bp" or "b.p." refers to boiling point, "mm of Hg" refers to pressure in millimeters of mercury, "cm" refers to centimeters, "nm" refers to nanometers, "$[\alpha]^{20}_D$" refers to specific rotation of the D line of sodium at 20° C. obtained in a 1 decimeter cell, "c" refers to concentration in g/mL, "THF" refers to tetrahydrofuran, "DMF" refers to dimethylformamide, "NMP" refers to 1-methyl-2-pyrrolidinone, "brine" refers to a saturated aqueous sodium chloride solution, "M" refers to molar, "mM" refers to millimolar, "µM" refers to micromolar, "nM" refers to nanomolar, "TLC" refers to thin layer chromatography, "HPLC" refers to high performance liquid chromatography, "HRMS" refers to high resolution mass spectrum, "CIMS" refers to chemical ionization mass spectrometry, "ESI" refers to electrospray ionization mass spectrometry, "$t_R$" refers to retention time, "lb" refers to pounds, "gal" refers to gallons, "L.O.D." refers to loss on drying, "µCi" refers to microcuries, "i.p." refers to intraperitoneally, "i.v." refers to intravenously.

In one aspect of this invention there is disclosed novel compounds having the general structure shown in formula I:

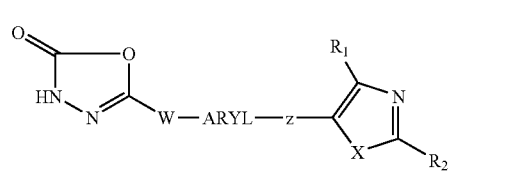

wherein
ARYL is phenyl or pyridinyl, wherein said phenyl or pyridinyl is optionally substituted with one or more substituents selected from the group consisting of halogen, $C_{1-6}$alkyl, $C_{2-6}$alkenyl, $C_{1-6}$alkoxy, $C_{1-6}$perfluoroalkyl; $C_{1-6}$alkylthio, hydroxy, hydroxy$C_{1-6}$alkyl, $C_{1-4}$acyloxy, nitro, cyano, $C_{1-6}$alkylsulfonyl, amino, $C_{1-6}$alkylamino and $C_{1-6}$alkoxycarbonyl;
W is a bond or $(CH_2)_m$, wherein m is an integer from 1 to 4;
Z is —O$(CH_2)_n$—, —SO$_2$$(CH_2)_n$—, —$(CH_2)_n$—Y—$(CH_2)_n$, —$(CH_2)_n$—CO—, —O$(CH_2)_n$—CO— or —$(CH_2)_n$—Y—$(CH_2)_n$—CO— wherein Y is NR$_3$, O or S and R$_3$ is selected from the group consisting of H, $C_{1-6}$alkyl, $C_{3-8}$cycloalkyl, $C_{1-6}$alkyl$C_{3-8}$cycloalkyl and benzyl and n is independently an integer from 1 to 5;
X is NR$_3$, O or S wherein R$_3$ is as defined above;
R$_1$ is H, halogen, $C_{1-6}$alkyl, $C_{1-6}$alkoxy, $C_{1-6}$perfluoroalkyl; hydroxy$C_{1-6}$alkyl, nitro, cyano, and $C_{1-6}$alkylamino; and
R$_2$ is substituted or unsubstituted phenyl, pyridinyl or thienyl wherein the substituents are selected from the group consisting of halogen, $C_{1-6}$alkyl, $C_{2-6}$alkenyl, $C_{1-6}$alkoxy, $C_{1-6}$perfluoroalkyl, $C_{1-6}$alkylthio, hydroxy, hydroxy$C_{1-6}$alkyl, $C_{1-4}$acyloxy, nitro, cyano, $C_{1-6}$alkylsulfonyl, amino, $C_{1-6}$alkylamino and $C_{1-6}$alkoxycarbonyl; or a stereoisomer, a tautomer or a solvate thereof or a pharmaceutically acceptable salt thereof.

In a further aspect of this embodiment, is disclosed a compound wherein ARYL is phenyl.

Compounds exemplary of this embodiment are selected form the group consisting of: 5-{4-[4-methyl-2-(4-trifluoromethyl-phenyl)-thiazol-5-ylmethoxy]-phenyl}-3H-[1,3,4]oxadiazol-2-one, 5-[4-(4-methyl-2-m-tolyl-oxazol-5-yl-methoxy)-phenyl]-3H-[1,3,4]oxadiazol-2-one, 5-{4-[4-methyl-2-(4-trifluoromethyl-phenyl)-thiazol-5-yl)-methoxymethyl]-phenyl}-3H-[1,3,4]oxadiazol-2-one, 5-{3-[4-methyl-2-(4-trifluoromethyl-phenyl)-thiazol-5-yl)-methoxymethyl]-phenyl}-3H-[1,3,4]oxadiazol-2-one, 5-{4-[4-butyl-2-(4-trifluoromethyl-phenyl)-thiazol-5-ylmethoxy]-2-chloro-phenyl}-3H-[1,3,4]oxadiazol-2-one, 5-{4-[4-butyl-2-(4-trifluoromethyl-phenyl)-thiazol-5-yl-methoxymethyl]-2-fluoro-phenyl}-3H-[1,3,4]oxadiazol-2-one, 5-{4-[4-butyl-2-(4-trifluoromethyl-phenyl)-thiazol-5-ylmethoxy]-benzyl}-3H-[1,3,4]oxadiazol-2-one, and 5-(2-{3-[4-butyl-2-(4-trifluoromethyl-phenyl)-thiazol-5-ylmethoxy]-phenyl}-ethyl)-3H-[1,3,4]oxadiazol-2-one.

In another aspect of this embodiment, is disclosed a compound wherein ARYL is phenyl and R$_2$ is phenyl.

In a further aspect of this embodiment, is disclosed a compound wherein ARYL is phenyl, Z is —O$(CH_2)_n$— and R$_2$ is phenyl.

In yet another aspect of this embodiment, is disclosed a compound wherein ARYL is phenyl, Z is —O(CH$_2$)$_n$—, X is O or S and R$_2$ is phenyl.

In another aspect of this embodiment, is disclosed a compound wherein ARYL is phenyl, Z is —O(CH$_2$)$_n$—, X is O or S, R$_1$ is C$_{1-6}$alkyl and R$_2$ is phenyl and W is a bond.

In a further aspect of this embodiment, is disclosed a compound wherein X is O.

In yet another aspect of this embodiment, is disclosed a compound wherein X is S.

In a further aspect of this embodiment, is disclosed a compound wherein ARYL is phenyl, Z is —(CH$_2$)$_n$—Y—(CH$_2$)$_n$— and R$_2$ is phenyl.

In yet another aspect of this embodiment, is disclosed a compound wherein ARYL is phenyl, Z is —(CH$_2$)$_n$—Y—(CH$_2$)$_n$—, X is O or S and R$_2$ is phenyl.

In another aspect of this embodiment, is disclosed a compound wherein ARYL is phenyl, Z is —(CH$_2$)$_n$—Y—(CH$_2$)$_n$—, X is O or S, R$_1$ is C$_{1-6}$alkyl and R$_2$ is phenyl and W is a bond.

In yet another aspect of this embodiment, is disclosed a compound wherein X is S.

In another aspect of this embodiment, is disclosed a compound wherein Y is O.

In a further aspect of this embodiment, is disclosed a compound wherein ARYL is phenyl, Z is —O(CH$_2$)$_n$— and R$_2$ is phenyl.

In yet another aspect of this embodiment, is disclosed a compound wherein ARYL is phenyl, Z is —O(CH$_2$)$_n$—, X is O or S and R$_2$ is phenyl, R$_1$ is C$_{1-6}$alkyl and R$_2$ is phenyl and W is (CH$_2$)$_m$ wherein m is an integer from 1 to 4.

In yet another aspect of this embodiment, is disclosed a compound wherein X is S.

In another embodiment of the present invention, is disclosed a pharmaceutical composition comprising an effective amount of a compound of formula I and a pharmaceutical acceptable carrier.

In another embodiment of the present invention, is disclosed method of treating a disease in a mammal wherein the disease is capable of being, modulated by PPARdelta ligand binding activity, which comprises administering to said mammal having said disease a therapeutically effective amount of a compound of formula I.

In a further aspect of this embodiment, is disclosed a method wherein said disease is a demyelinating disease selected form the group consisting of multiple sclerosis, Charcot-Marie-Tooth disease, Pelizaeus-Merzbacher disease, encephalomyelitis, neuromyelitis optica, adrenoleukodystrophy, Guillian-Barre syndrome and disorders in which myelin forming glial cells are damaged including spinal cord injuries, neuropathies and nerve injury.

In another aspect of this embodiment, is disclosed a method wherein the demyelinating disease is multiple sclerosis.

In still another aspect of this invention is disclosed a method wherein said disease is selected from the group consisting of obesity, hypertriglyceridemia, hyperlipidemia, hypoalphalipoproteinemia, hypercholesterolemia, dyslipidemia, Syndrome X, Type II diabetes mellitus and complications thereof selected from the group consisting of neuropathy, nephropathy, retinopathy and cataracts, hyperinsulinemia, impaired glucose tolerance, insulin resistance, atherosclerosis, hypertension, coronary heart disease, peripheral vascular disease or congestive heart failure.

The compounds disclosed herein can be synthesized according to the following procedures of Schemes, wherein the X, and R substituents are as identified for formula (I), above unless otherwise noted. It being understood that certain starting materials in the synthetic schemes would be commercially available or whose synthesis would be obvious to those skilled in the art.

If necessary, in the following synthetic schemes, reactive functional groups present in the compounds described in this invention may be protected by suitable protecting groups. The protecting group may be removed at a later stage of the synthesis. Procedures for protecting reactive functional groups and their subsequent removal may be found in T. W. Greene and P. G. M. Wuts, *Protective Groups in Organic Synthesis*, Wiley and Sons, 1991.

Scheme A shows the synthesis of the appropriate imidazole, oxazole or thiazole, intermediates for compounds of formula I wherein X is O, S, NR$_3$. The heterocycles can be prepared using methods known in the chemical literature (for reviews see Katritzky, A. R.; Rees, C. W. Eds. *Comprehensive Heterocyclic Chemstry*, Vol. 5; Pergamon Press (1984); Katritzky, A. R.; Rees, C. W.; Scriven, E. F. V. Eds. *Comprehensive Heterocyclic Chemistry II*; Vols 3 & 4, Pergamon Press (1996)). Specifically, said oxazoles, imidazoles and thiazoles can be prepared by fusion of an appropriate α haloketone 1, respectively, with an amide, amidine or a thioamide (general formula 2), at temperatures ranging from about 40° C. to 150° C. to give the intermediate heterocycles 3.

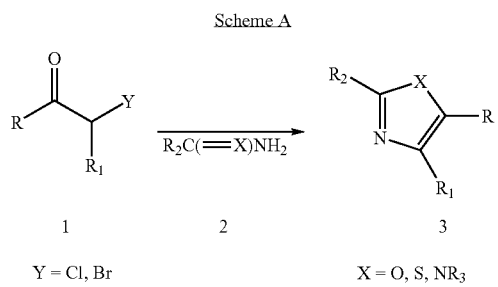

Scheme A

Y = Cl, Br                X = O, S, NR$_3$

In Scheme B the general synthesis of compounds of formula I wherein Z is —O(CH$_2$)$_n$— is shown. Accordingly, in Step B1 the appropriately substituted carboxylic acid ester 4, which can be synthesized as illustrated in Scheme A is reduced to the alcohol 5 by methods that are well known in the art. For example, the reduction may be effected by aluminum hydrides such as lithium aluminum hydrides or diisobutylaluminum hydride in an inert solvent. In Step B2, the alcohol functional group in compound 5, is converted to a leaving group to give compound 6, wherein Lg is a leaving group such as halogen, or sulfonate esters, for example mesylates or tosylates. Conversion to the leaving group can be accomplished by reaction of the alcohol with reagents such N-bromosuccinimide in the presence of triphenylphosphine to produce a compound wherein the leaving group is bromide, or reaction with thionyl chloride to give a compound wherein the leaving group is chloride. If a sulfonate ester is desired, reaction of compound 5 with an appropriate sulfonyl chloride in the presence of a suitable base would produce the desired sulfonate ester. For example, reaction of compound 5 with methanesulfonyl chloride in the presence of an organic base such as triethylamine or pyridine in an inert solvent would give compound 6 wherein the leaving group is OSO$_2$CH$_3$.

In Step B3 an appropriately substituted hydroxy aryl ester, 7 is reacted with the heterocycle, 6 to displace the leaving group to afford coupled ester, 8. The displacement reaction is run under conditions well known in the art. Typically the reaction is run in the presence of a base such as sodium hydride or other inorganic bases such as alkali carbonates or alkali hydroxides in an inert solvent. The temperature of the reaction, although not critical, is from 0° C. to the reflux temperature of the inert solvent.

Compound 8, in Step B4 is then treated with hydrazine either neat or in a suitable organic solvent at elevated temperatures to give the acid hydrazide, 9. Typically, the reaction is run at a temperature of between 50° C. and the reflux temperature of the organic solvent.

Cyclization of the acid hydrazide 9, in Step B5, to the target 1,3,4-oxadiazol-2-ones 10 is accomplished by treatment of compound 9 with a chloroformate in the presence of an organic base such as pyridine followed by treatment with strong, hindered amine base such as 1,8-diazabicyclo[5.4.0]undec-7-ene (DBU) in a suitable organic solvent such as acetonitrile in a sealed tube at elevated temperature. Typically, the reaction can be run from 100° C. to 200° C. The 1,3,4-oxadiazol-2-ones may also be synthesized by reacting compound 9 with phosgene. See Stempel, A., et al., *J. Org. Chem.* 1955, 20, 412.

In Step B6, an alternative synthesis of the coupled ester, 8 is illustrated. Accordingly, the alcohol, 5 can be reacted with the hydroxyaryl ester, 8 in the presence of a triaryl or trialkylphosphine, such as triphenylphosphine or tri-n-butylphosphine and diethylazodicarboxylate in an inert solvent, for example THF or dichloromethane to afford the coupled ester 8. Typically the reaction is run at a temperature between room temperature and the reflux temperature of the inert solvent.

Scheme C illustrates the synthesis of the compound of formula I wherein Z is —$(CH_2)_n$—Y—$(CH_2)_n$—. The scheme is most useful to synthesize compounds wherein n represents 1 or 2 in the alkylene chain attached to ARYL. In Step C1 compound 5 (Y=O) is converted to compound 6 (wherein Lg is chloro or bromo) as described in Scheme B, Step B2. Compound 6 is then reacted with thiourea, compound 11, under conditions similar to those found in Treau, M. et al. *Heterocycles*, 2001, 55 (9), 1727-1735, to produce the thiol, 5a.

When compound 6 is reacted with a primary amine 12, the aminoalkyl heterocycle 5b is produced. This displacement of a leaving group by an amine is well known to those skilled in the art. Typically, the displacement reaction is run in a polar organic solvent in the presence of an organic base that acts as an acid scavenger. Although not critical, the displacement reaction is run at a temperature of between ambient to reflux temperature of the solvent.

In Step C3 compounds 5, 5a and 5b can be reacted with compound 13 to afford the coupled arylester, 14, wherein Y is O, S or $NR_3$. Thus, when compounds 5 (Y=O) and 5a (Y=S) are reacted with 13 to displace the leaving group, the reaction will typically be run in the presence of a strong base, for example sodium hydride, in a polar aprotic solvent, such as DMF or DMSO at temperatures of about between 0° C. to

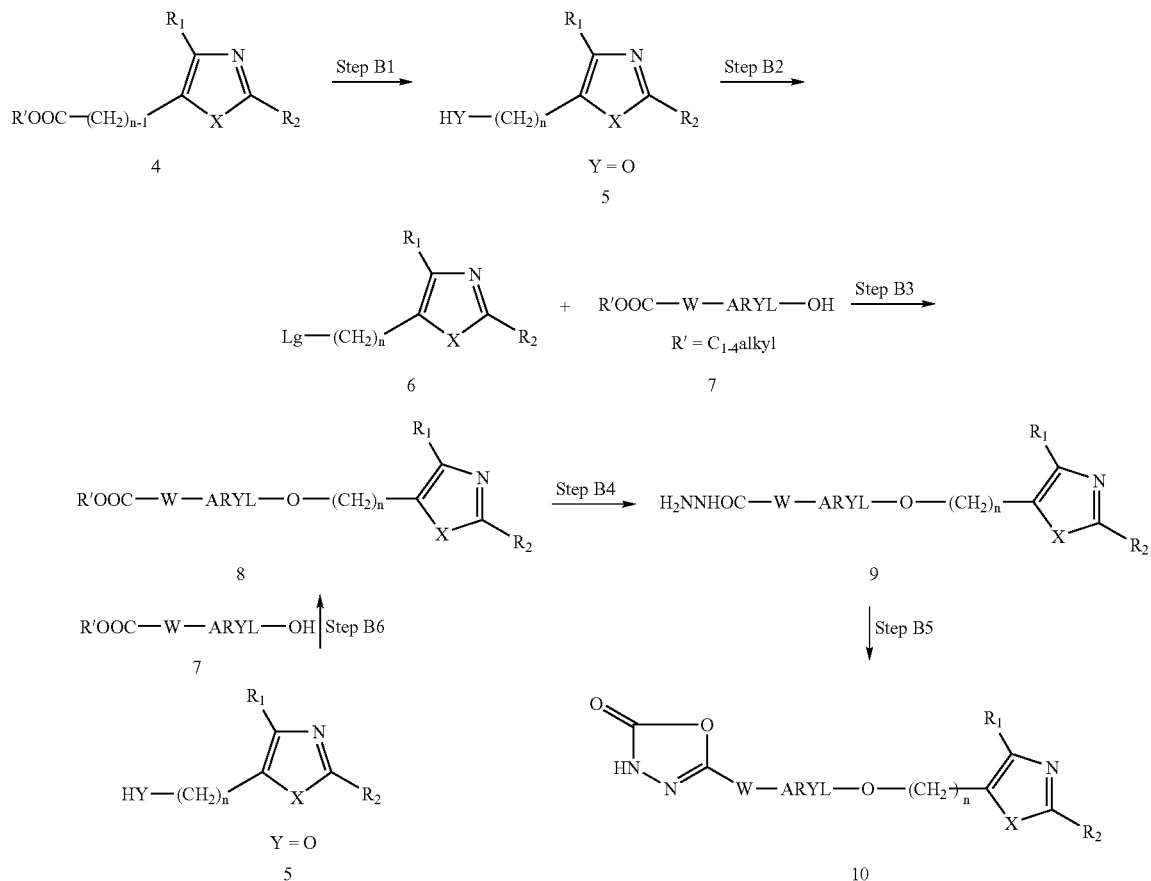

Scheme B

150° C. When compound 5b (Y=NR₃) is reacted with 14, conditions identical to those described above in Step C2 for the primary amine are used.

Synthesis of the desired 1,3,4-oxadiazol-2-ones 16, from compound 14 is accomplished in the two steps (C4 and C5) exactly as described in Scheme B, Steps B4 and B5.

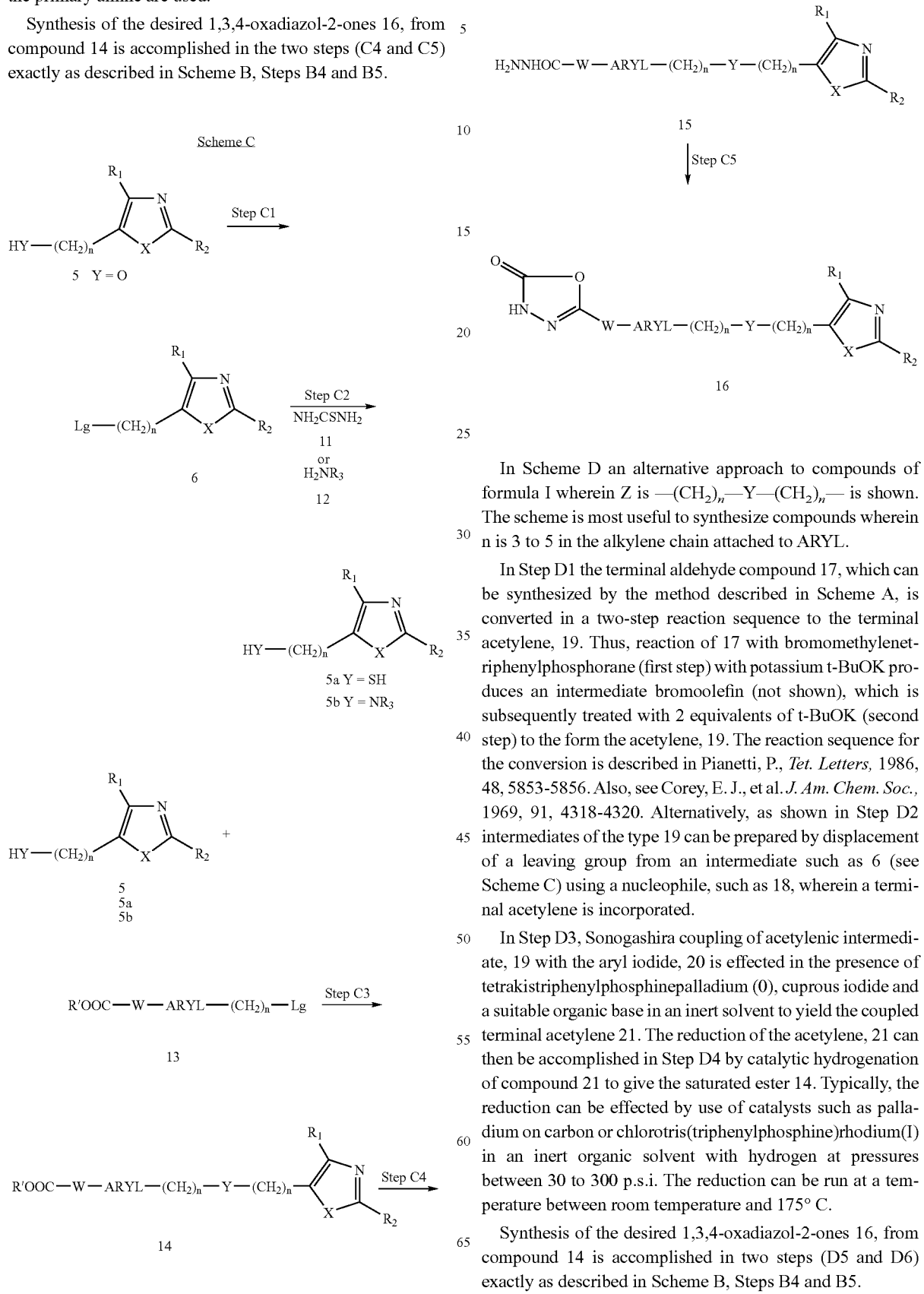

In Scheme D an alternative approach to compounds of formula I wherein Z is —(CH₂)ₙ—Y—(CH₂)ₙ— is shown. The scheme is most useful to synthesize compounds wherein n is 3 to 5 in the alkylene chain attached to ARYL.

In Step D1 the terminal aldehyde compound 17, which can be synthesized by the method described in Scheme A, is converted in a two-step reaction sequence to the terminal acetylene, 19. Thus, reaction of 17 with bromomethylenetriphenylphosphorane (first step) with potassium t-BuOK produces an intermediate bromoolefin (not shown), which is subsequently treated with 2 equivalents of t-BuOK (second step) to the form the acetylene, 19. The reaction sequence for the conversion is described in Pianetti, P., *Tet. Letters,* 1986, 48, 5853-5856. Also, see Corey, E. J., et al. *J. Am. Chem. Soc.,* 1969, 91, 4318-4320. Alternatively, as shown in Step D2 intermediates of the type 19 can be prepared by displacement of a leaving group from an intermediate such as 6 (see Scheme C) using a nucleophile, such as 18, wherein a terminal acetylene is incorporated.

In Step D3, Sonogashira coupling of acetylenic intermediate, 19 with the aryl iodide, 20 is effected in the presence of tetrakistriphenylphosphinepalladium (0), cuprous iodide and a suitable organic base in an inert solvent to yield the coupled terminal acetylene 21. The reduction of the acetylene, 21 can then be accomplished in Step D4 by catalytic hydrogenation of compound 21 to give the saturated ester 14. Typically, the reduction can be effected by use of catalysts such as palladium on carbon or chlorotris(triphenylphosphine)rhodium(I) in an inert organic solvent with hydrogen at pressures between 30 to 300 p.s.i. The reduction can be run at a temperature between room temperature and 175° C.

Synthesis of the desired 1,3,4-oxadiazol-2-ones 16, from compound 14 is accomplished in two steps (D5 and D6) exactly as described in Scheme B, Steps B4 and B5.

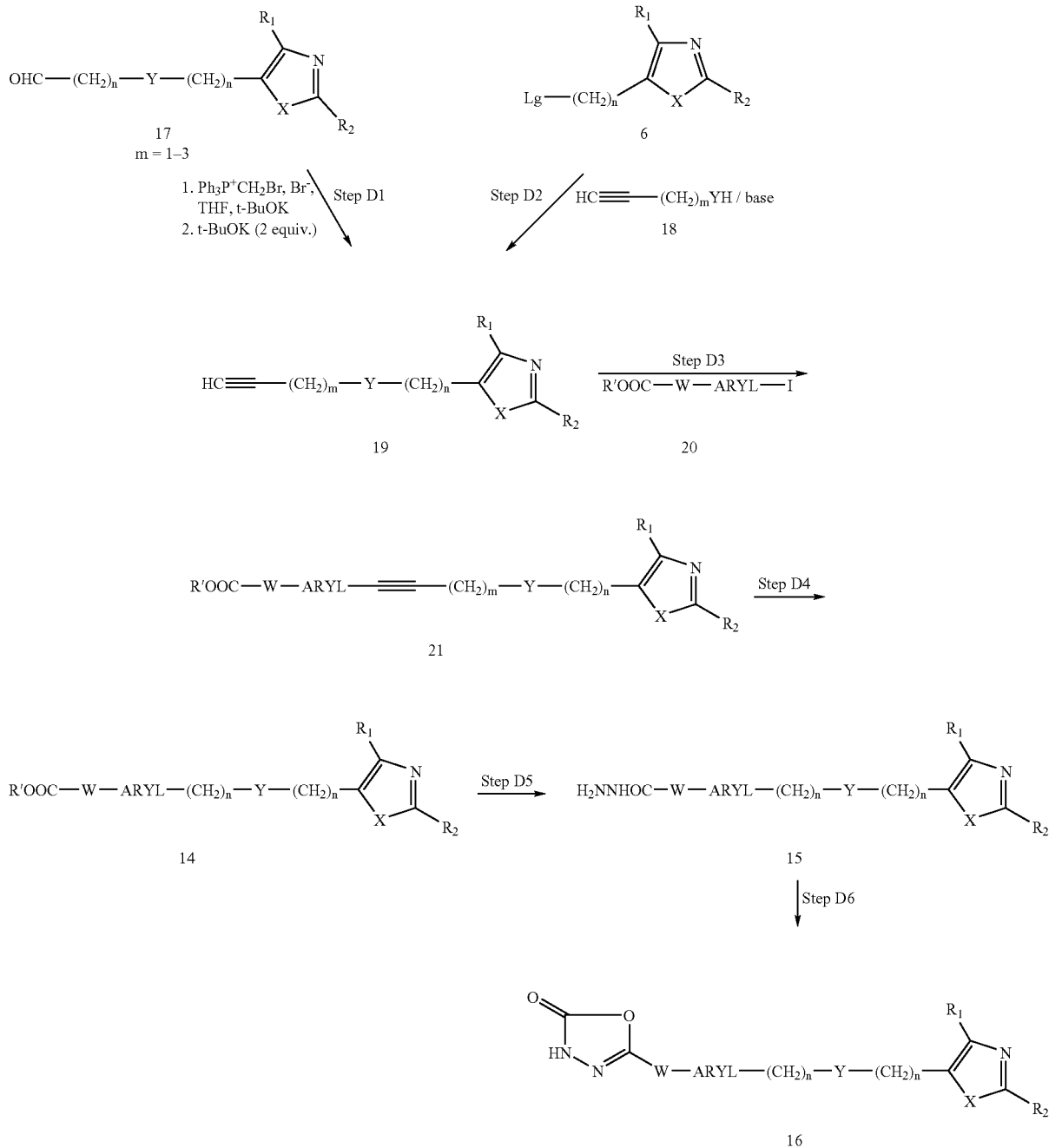

Scheme E illustrates a particular synthesis of compounds of formula I wherein Z is —(CH$_2$)$_n$NR$_3$(CH$_2$)$_n$—. In this approach, the linker Z is constructed by a reductive amination of an aldehyde with an amine. For example, in Step E1 treatment of 5b (wherein Y=NR$_3$) with an aldehyde, such as 4-formyl-benzoic acid methyl ester (n=1), compound 22, in a polar solvent, usually an alcohol or an alcohol THF mixture, followed by treatment with a reducing agent such as sodium triacetoxy-borohydride provides the required intermediate 14a (n=1).

Similarly in Step E2, treatment of an aldehyde such as 17a as with an amine, such as 4-aminoalkyl benzoic acid methyl ester (n=1), compound 23, provides 14a, wherein n is 1 and R$_3$ is H for —(CH$_2$)$_n$NR$_3$. Compound 14a in steps E3 and E4 is converted to 1,3,4,-oxadiazol-2-ones 16a as described in Scheme B, Steps B4 and B5.

More generally, appropriate amines (R'OOC-ARYL-(CH$_2$)$_n$NHR$_3$) are prepared from the corresponding nitriles or nitro compounds by catalytic hydrogenation or from acetylenic amines and an aryl iodide or bromide by Sonogashira coupling followed by catalytic hydrogenation as described in Scheme D.

Scheme E

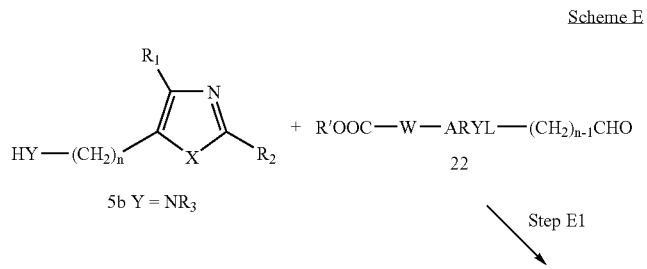

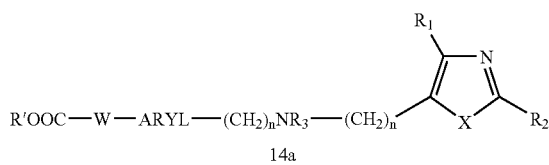

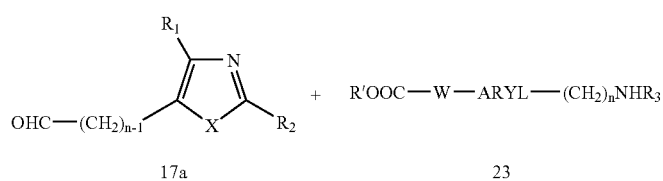

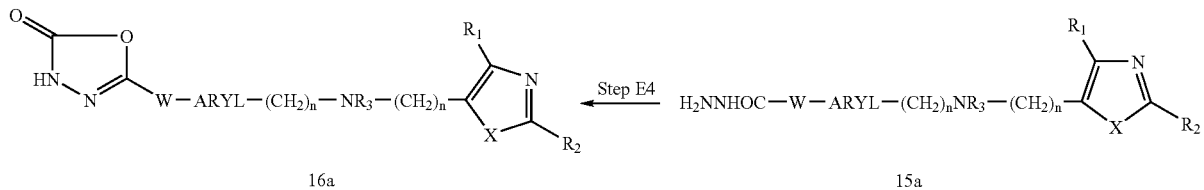

Scheme F illustrates the synthesis of compounds of formula I wherein Z is —SO$_2$(CH$_2$)$_n$—. In Step F1 treatment of an aryl sulfonyl chloride, 24 with aqueous sodium sulfite provides the sulfinic acid, 25. Reaction of 25, as in Step F2, with an intermediate such as 6 in a polar solvent such as DMF, acetonitrile or ethanol in the presence of a base such as DBU, pyridine, sodium methoxide or sodium hydroxide provides intermediate 26. Intermediate 26 is converted to the corresponding 1,3,4-oxadiazol-2-one, 28 in Steps F3 and F4 as illustrated in Scheme B, Steps B4 and B5.

Scheme F

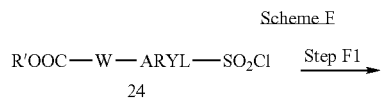

-continued

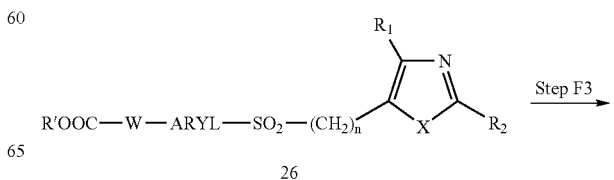

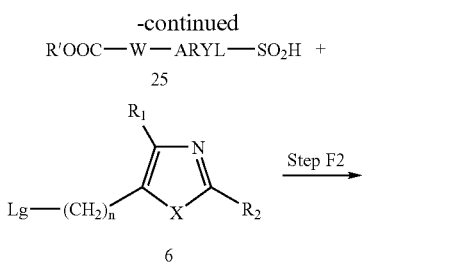

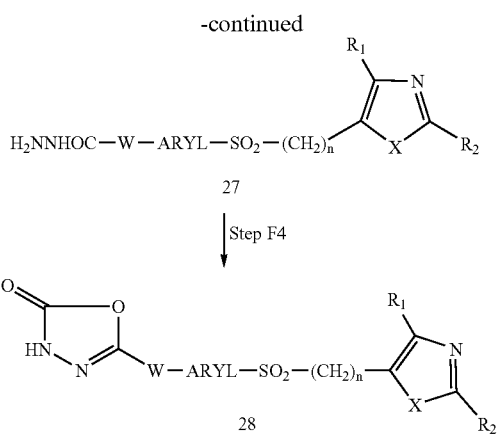

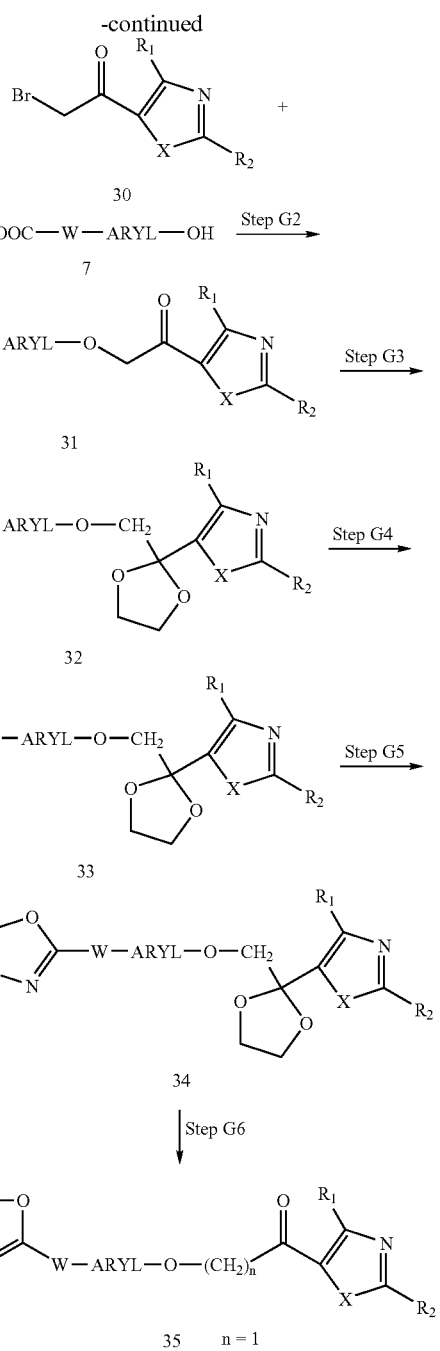

Scheme G illustrates the synthesis of compound of formula I wherein Z is —O(CH$_2$)$_n$CO—. The scheme illustrates the case wherein n is 1. The starting 2-acyl heterocycle, 29 can be synthesized from the corresponding carboxylic acid (prepared by the method illustrated in Scheme A) by addition of an appropriate Grignard reagent to an intermediate N-methoxy N-methyl carboxamide (Khlestkin, V. K. et al.; Current Organic Chemistry, 2003, 7(10), 967-993. and Singh, J. et al., Journal für Praktische Chemie, 2000, 342, 340-347). Preparation of the intermediate N-methoxy-N-methyl carboxamide is most conveniently carried out by reaction of the acid with N-methoxy-N-methyl hydroxylamine hydrochloride in the presence of a peptide coupling reagent such as EDC, DCC, DMPU and a tertiary amine base such as diisopropylethylamine or triethylamine.

Thus in hand, 29 is brominated to produce the bromoketone 30, as shown in Step G1. The bromination can be accomplished by well-known methods, for example reaction of 29 with pyridinium bromide per bromide in acetic acid or reaction of 29 with Br$_2$ in an inert organic solvent such as dichloromethane. The resulting bromoketone 30, in Step G2, is reacted with the arylhydroxy ester 7 under conditions described in Scheme B (Step B3) to afford the coupled ester 31. The ketone functionality in 31 is protected as a ketal 32, as shown in Step G3 by methods well known in the art. Compound 32 is then converted to the 1,3,4-oxadizol-2-one ketal 34, in Steps G4 to G5 by the standard sequence as described in Scheme B (B4 and B5). Finally, in Step G6, the ketal functionality in 34 is cleaved, for example, with mineral acid in THF-methanol-water or other methods known in the art to afford the target structure 35.

It would be evident to one skilled in the art that the above procedure of Scheme G could be used to synthesize analogs where n is 2-5 for compound 35 by starting with a bromoketone, compound 30, with a larger bromoalkanoyl substituent (Br(CH$_2$)$_n$CO—, wherein n is 2 to5).

Scheme H illustrates the procedure for the preparation of compounds of formula I wherein Z is —(CH$_2$)$_n$CO—. In Step H1, the appropriate methoxycarbonyl-substituted heterocycle, 36 is treated with 2 equivalents of the lithium enolate of t-butylacetate in a solvent such as THF or DME at a temperature ranging from −78° C. to room temperature to provide the ketoacetate intermediate 37. In Step H2, treatment of 37 with a base such as sodium hydride in an inert solvent at a temperature between −10° C. and room temperature followed by alkylation of the resulting anion with an electrophile such as 13 yields the advanced intermediate ketodiester 38. The decarboxylation shown in Step H3 and can be accomplished by first treatment of 38 with TFA in an inert solvent such as Scheme G

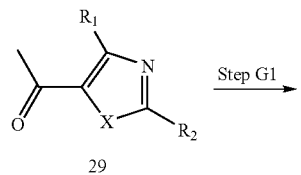

dichloromethane followed by thermolysis at a temperature between 70° C. and 150° C. to provide intermediate ketoester 39. The ketone functionality in 39 is protected as a ketal 40, as shown in Step H4 by methods well known in the art. Compound 40 is then converted to the 1,3,4-oxadiazol-2-one ketal 42 in Steps H5 to H6 by the standard sequence as described in Scheme B (B4 and B5). Finally, in Step H7, the ketal functionality in 42 is cleaved, as described above in Scheme G, Step G6 to afford the desired 1,3,4-oxadiazol-2-one, compound 43.

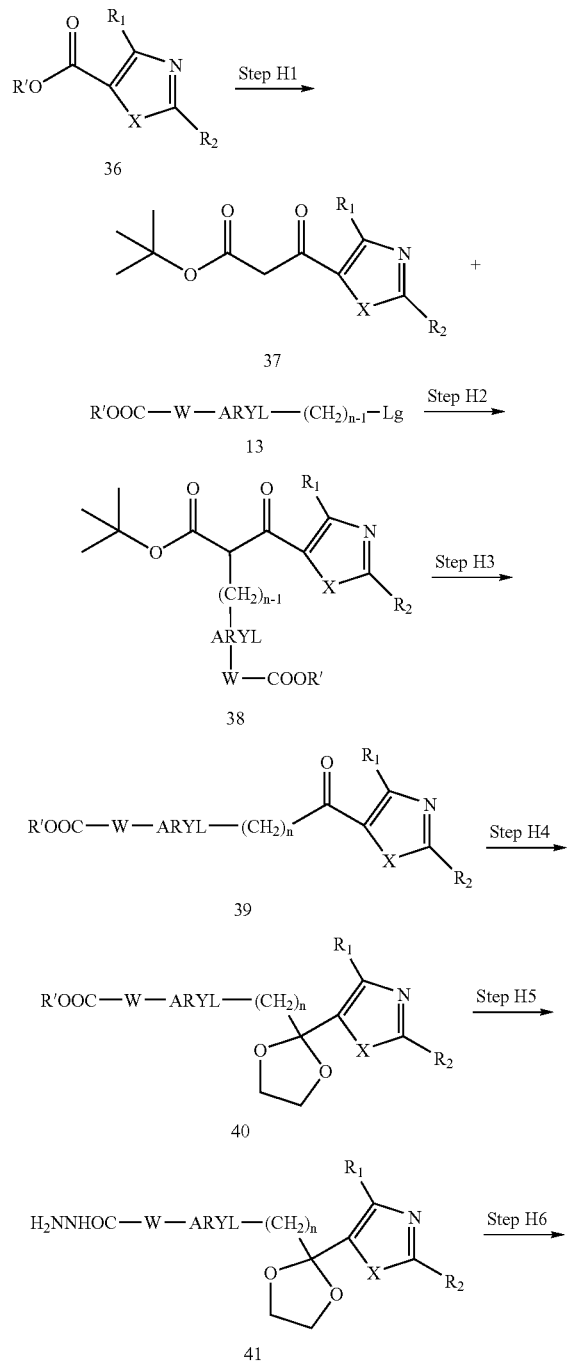

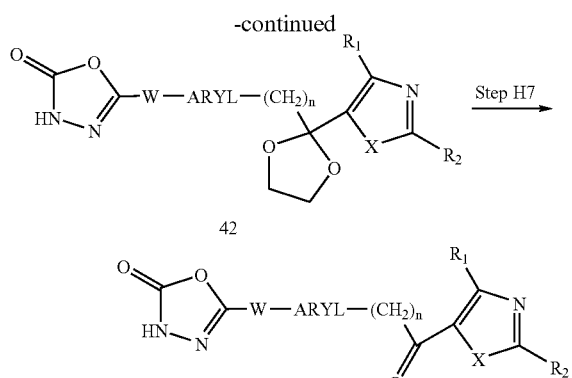

BIOLOGICAL EXAMPLES

The following test protocols are used to ascertain the biological properties of the compounds of this invention. The following examples are being presented to further illustrate the invention. However, they should not be construed as limiting the invention in any manner.

Determination of $EC_{50}$ Values in the Cell Based PPARdelta-GAL4 Assay

Principle

The potency of substances, which bind to human PPAR delta and activate it in an agonistic manner, is analyzed using a stably transfected HEK cell line (HEK=human embryo kidney) which is referred to here as PPAR delta reporter cell line. The PPAR delta reporter cell line contains two genetic elements, a luciferase reporter element (pdeltaM-GAL4-Luc-Zeo) and a PPAR delta fusion protein (GR-GAL4-humanP-PAR delta-LBD), which mediates expression of the luciferase reporter element depending on a PPAR delta ligand. The stably and constitutively expressed fusion protein GR-GAL4-humanPPAR delta-LBD binds in the cell nucleus of the PPAR delta reporter cell line via the GAL4 protein portion to the GAL4 DNA binding motifs 5'-upstream of the luciferase reporter element which is stably integrated in the genome of the cell line. There is only little expression of the luciferase reporter gene in the absence of a PPAR delta ligand if fatty acid-depleted fetal calf serum (cs-FCS) is used in the assay. PPAR delta ligands bind and activate the PPAR delta fusion protein and thereby stimulate expression of the luciferase reporter gene. The luciferase, which is formed can be detected by means of chemiluminescence via an appropriate substrate.

Construction of the PPAR Delta Reporter Cell Line:

The production of the stable PPAR delta reporter cell line is based on a stable HEK-cell clone which was stably transfected with a luciferase reporter element. This step was already described above in the section "construction of the PPAR alpha reporter cell line". In a second step, the PPAR delta fusion protein (GR-GAL4-humanPPAR delta-LBD was stably introduced into this cell clone. For this purpose, the cDNA coding for the N-terminal 76 amino acids of the glucocorticoid receptor (Accession # P04150) was linked to the cDNA section coding for amino acids 1-147 of the yeast transcription factor GAL4 (Accession # P04386). The cDNA of the ligand-binding domain of the human PPAR delta receptor (amino acids S139-Y441; Accession # L07592) was cloned in at the 3'-end of this GR-GAL4 construct. The fusion construct prepared in this way (GR-GAL4-humanPPAR delta-LBD) was recloned into the plasmid pcDNA3 (Invitrogen) in order to enable constitutive expression by the cytomegalovirus promoter. This plasmid was linearized with a restriction endonuclease and stably transfected into the previously described cell clone containing the luciferase reporter element. The resulting PPAR delta reporter cell line which contains a luciferase reporter element and constitutively expresses the PPAR delta fusion protein (GR-GAL4-human PPAR delta-LBD) was isolated by selection with zeocin (0.5 mg/ml) and G418 (0.5 mg/ml).

Assay Procedure and Evaluation:

The activity of PPAR delta agonists is determined in a 3-day assay, which is described below:

Day 1

The PPAR delta reporter cell line is cultivated to 80% confluence in DMEM (# 41965-039, Invitrogen) which is mixed with the following additions: 10% cs-FCS (fetal calf serum; #SH-30068.03, Hyclone), 0.5 mg/ml zeocin (#R250-01, Invitrogen), 0.5 mg/ml G418 (#10131-027, Invitrogen), 1% penicillin-streptomycin solution (#15140-122, Invitrogen) and 2 mM L-glutamine (#25030-024, Invitrogen). The cultivation takes place in standard cell culture bottles (# 353112, Becton Dickinson) in a cell culture incubator at 37° C. in the presence of 5% $CO_2$. The 80%-confluent cells are washed once with 15 ml of PBS (#14190-094, Invitrogen), treated with 3 ml of trypsin solution (#25300-054, Invitrogen) at 37° C. for 2 min, taken up in 5 ml of the DMEM described and counted in a cell counter. After dilution to 500.000 cells/ml, 35,000 cells are seeded in each well in a volume of 180 µL of a 96 well microtiter plate with a clear plastic base (#3610, Corning Costar). The plates are incubated in the cell culture incubator at 37° C. and 5% $CO_2$ for 24 h.

Day 2

PPAR delta agonists to be tested are dissolved in DMSO in a concentration of 10 mM. This stock solution is diluted in DMEM (#41965-039, Invitrogen) which is mixed with 5% cs-FCS (#SH-30068.03, Hyclone), 2 mM L-glutamine (#25030-024, Invitrogen) and the previously described antibiotics (zeocin, G418, penicillin and streptomycin). Test substances are tested in 11 different concentrations in the range from 10 µM to 100 pM. More potent compounds are tested in concentration ranges from 1 µM to 10 pM or between 100 nM and 1 pM.

The medium of the PPAR delta reporter cell line seeded on day 1 is completely is either completely removed by aspiration or not, and the test substances diluted in medium are immediately added to the cells. The dilution and addition of the substances is carried out by a robot (Beckman FX). The final volume of the test substances diluted in medium is 100 µl per well of a 96 well microtiter plate. The DMSO concentration in the assay is less than 0.1% v/v in order to avoid cytotoxic effects of the solvent.

Each plate was charged with a standard PPAR delta agonist, which was likewise diluted in 11 different concentrations, in order to demonstrate the functioning of the assay in each individual plate. The assay plates are incubated in an incubator at 37° C. and 5% $CO_2$ for 24 h.

Alternatively, 20 µL of a 10× final concentration of the test substance is added directly to the 180 µL containing the plated cells. The test substances are tested in 8 different concentrations, in triplicate, in this assay plate set-up.

Day 3

The PPAR delta reporter cells treated with the test substances are removed from the incubator, and the medium is aspirated off. The cells are lyzed by pipetting 50 µl of Bright Glo reagent (from Promega) into each well of a 96 well microtiter plate. After incubation at room temperature in the dark for 10 minutes, the microtiter plates are measured in the luminometer (Trilux from Wallac). The measuring time for each well of a microtiter plate is 1 sec.

Evaluation:

The raw data from the luminometer are transferred into a Microsoft Excel file. Dose-effect plots and $EC_{50}$ values of PPAR agonists are calculated using the XL.Fit program as specified by the manufacturer (IDBS).

PPARdelta $EC_{50}$ values in the range of 1 nM to >10 µM were measured for the PPAR modulators of the examples in this application. Compounds of the invention of formula I can act as agonists or antagonists. The assay to determine partial agonist or antagonist activity is described below.

Determination of Effectiveness of Partial Agonists or Antagonists at the PPARdelta Receptor This assay determines if compounds act as partial agonists or antagonists at the PPARdelta receptor.

The plating and harvesting of the assay plates is as described in Day 1 and 3 above.

Day 2

The partial agonist or antagonist and a known selective agonist are diluted in DMEM (#41965-039, Invitrogen), which is mixed with 10% cs-FCS (#SH-30068.03, Hyclone), 2 mM L-glutamine (#25030-024, Invitrogen) and the previously described antibiotics (zeocin, G418, penicillin and streptomycin) to 20× desired final concentrations. Ten microliters of the partial agonist or antagonist is added to the cell-containing assay plate. The assay plates are incubated in an incubator at 37° C. and 5% $CO_2$ for 30 minutes. Ten microliters of the 20× known selective agonists are then added, after the partial agonist or antagonist pre-incubation. The assay plates are incubated in an incubator at 37° C. and 5% $CO_2$ for 24 h. The effect on the known selective agonists $EC_{50}$'s is determined for each partial agonist or antagonist concentration.

SPA PPAR Delta-LBD Binding Assay

Stock Solutions:
  1 M Tris (pH=8.0 or pH=7.6)(Gene Medicine Stock Room)
  2 M KCl (Powder in N2140)
  Tween 20
  100 mM DTT
  13.9 □M GW2331 in EtOH HOT
  10 mM GW 2331 in DMSO COLD
  PPAR-alpha (Conc. varies)
  Ex: 0.884 □g/□l

| Wash Buffer: (Store at 4° C. Buffer is good for one week) | |
|---|---|
| 10 mM Tris(pH = 7.6 or 8) | 10 ml |
| 50 mM KCl | 25 ml |
| 0.05% Tween 20 | 0.5 ml |
| Millipore Water | 964.5 |

Check PH = 7.6

| Binding Buffer: (Prepare fresh binding buffer every time) | |
| --- | --- |
| Wash Buffer | 50 ml |
| 10 mM DTT | 5.5 ml |

Preparation of Reaction Reagents for 1 Plate:

Glutathione Coated SPA Beads
Each SPA bead bottle contains 500 mg beads
Reconstitute 500 mg of SPA beads in 5 ml of wash buffer, and will be good for few weeks
Store at 4° C.

Prepare Diluted SPA Beads in the Binding Buffer.
Adding 1 ml of above reconstituted SPA beads to 60 ml of Binding buffer adding 20 μl of above diluted beads to each well of a 96-well plate.
Use 2 ml of above diluted beads for each plate (no dead volume included).
3H GW-2331 plus GST-PPAR delta-LBD (for one 96-well plate no dead volume) 13.9 μM 40 nM/well
3.0 ml/plate (Including dead volume)
If 3H-GW2331 specific activity is 1 mci/ml (From Amersham), dilute 17 μl of 3H GW-2331 into 3.0 ml of Binding Buffer=0.08 μM
If protein concentration is 1 mg/mL, add 21 μl of proteins into 3.0 ml of binding buffer.
In Summary: ONE 96-well plate: 3000 μL Binding Buffer+ 17 μL of 3H-GW2331+21 μL of GST-PPAR-delta(1 mg/ml)

Control Plates

A 96-Well Mother Plate(For 2 Control Plates)

In Column #1:
Add 5 μl of cold GW2331(10 mM) to the wells E-H.
Add 45 μL of DMSO to the wells A-H.

In Column #12 (3-Fold Dilution):
Add 10 μL of cold GW2331(10 mM) to the well A.
then add 90 μl of DMSO to the well A, mix well the solution.
add 20 μl of DMSO to the wells B-H.
take 10 μl solution from the well A to B, mix well,
then take 10 μl solution from B to C, mix well,
then take 10 μl solution from C to D, mix well.
. . .
Finally, take 10 μl from F to H.

A Control Plate (for 8 Reaction Plates)
A control plate is 1:10 dilution of the mother plate. The dilution buffer is the wash buffer.

Sample Plates
To fresh CPC library plate, add 90 μl of DMSO
Take 10 μl of DMSO dilution and add it to 90 μl of wash buffer in a sample plate Reaction Plates:
Add 20 μl of SPA beads and 30 μl of 3H-GW2331 with GST-PPAR-delta to each well of a Reaction Plate.
Add 5 μl compounds from each well of the sample plate into columns 2 to 11 of a reaction plate.
Add 5 μl compounds from column 1 and column 12 of the control plate to the column 1 and column 12 of the reaction plate.

96-Well SPA Protocol:
Let reaction plates equilibrate for 20 minutes to 2 hours.
Seal the plates before counting in a Microbeta counter (Wallac).
Calculate $IC_{50}$.
In the SPA PPAR delta-LBD Binding Assay $IC_{50}$ values in the range of 1 nM to >10 μM were measured for the PPAR modulators of the examples in this application. Compounds of the invention of formula I can act as agonists or antagonists.

RAT/MICE Oligodendrocyte Cultures

Preparation of Cells:
1. Primary rat oligodendrocyte progenitor cells are obtained from the neocortex of newborn (postnatal days 2-3) rats or mice and are enriched, after removal of microglia, by mechanical separation from the astrocytic monolayer using a modification of the technique originally described by McCarthy and de Vellis (1980).
2. Remove the meninges from neonatal rat brain and mechanically dissociate tissue. Plate cells on T75 flasks and feed cells with DMEM/F12+10% FBS.
3. Collect oligodendrocytes growing on the astrocyte bed layer by shaking-off method fourteen days after the original prep date. Centrifuge the suspension and resuspend the cell pellet in serum free media (SFM; DMEM combined with 25 μg/ml transferring, 30 nM triiodothyronine, 20 nM hydrocortisone, 20 nM progesterone, 10 nM biotin, 1× trace elements, 30 nM selenium, 1 μg/ml putrescine, 0.1% BSA, 5 U/ml PenStrep, 10 μg/ml insulin) supplemented with the following growth factors: Platelet derived growth factor-AA (PDGF) and fibroblast growth factor-2 (FGF).
4. Plate the cells on PDL-coated dishes and incubate at 37° C. with 6-7% CO2.
5. Media components are replaced every 48 hr to keep the cells in a progenitor state.

Progenitor Cell Passaging to Increase Cell Numbers for Screening Assays:
1. When the culture are confluent, rinse the culture with PBS, add trypsin and incubate for ~2-3 min at 37° C.
2. Neutralize and centrifuge the cell suspension at 900 g for 5 min.
3. Resuspend the cell pellet in SFM+PDGF/FGF.
4. Feed the cells with fresh growth factors every 48 hrs to keep enrich for rapidly dividing progenitor cells.
5. Cells are passaged no more than 4-5 times prior to experimental assays.
6. All experiments involving oligodendrocyte progenitor cells were done using cells that were continuously maintained under these conditions. Greater than 95% of all cells were A2B5 immunopositive and expressed 2'3'-cyclic nucleotide 3'-phosphodiesterase II mRNA.
7. To generate mature oligodendrocytes, 24 h after plating progenitor cells were switched to SFM supplemented with or without IGF-I and grown under these conditions for 7 d prior to experimental assays.
8. Alternatively, the enriched rat Central Glia-4 (CG4) progenitor cell line may be used, which is maintained in base media (DMEM, with 2 mM glutamine, 1 mM sodium pyruvate, biotin (40 nM), insulin (1 μM) and N1) supplemented with 30% conditioned media from the B-104 neuroblastoma cell line. To induce differentiation, CG4 cells are switched to base media with 1% fetal calf serum (removed after 2 days) and insulin (500 nM).

A2B5 and MBP immunoreactivity is used to confirm >95% enrichment in immature and mature cultures, respectively.

Rat/Mouse Culture Compound Treatment:
1. Put 10,000-15,000 cells/well in 24-well PDL coated plates and culture the cells in presence of mitogen (10 ng/ml) overnight.
2. In the presence of mitogen:
   a. Next day, remove the old medium and add compounds in fresh medium (with mitogen)
   b. Compound dose response evaluations are performed at 6 different concentrations (10 □M, 1 □M, 100 nM, 10 nM, 1 nM, and 0.1 nM);
   c. Triplicates wells are run for each compound concentration.
3. In the absence of mitogen:
   a. Next day, remove the old medium and add compounds in fresh medium (without mitogen)
   b. Compound dose response evaluations are performed at 6 concentrations (10 □M, 1 □M, 100 nM, 10 nM, 1 nM, and 0.1 nM);
   c. Triplicates wells are run for each compound concentration.
4. Culture the treated cells for 7 d prior to using in experimental assays.

HUMAN Oligodendrocyte Cultures

Preparation of Cells:
1. Human neurospheres collected from E19.5-E22 human embryo cortex) are cultured for 2 weeks in progenitor media: DMEM/F12 containing 100 µg/ml transferring, 30 nM triiodothyronine, 20 nM hydrocortisone, 20 nM progesterone, 10 nM biotin, 1× trace elements, 30 nM selenium, 60 uM putrescine, 0.1% BSA, 5 U/ml Pen-Strep, 25 µg/ml insulin) supplemented with PDGF and FGF.
2. Neurospheres are dissociated with 20 U/ml papain at 37° C. for 30-50 min.
3. Cells are plated onto PDL coated dishes at density of 50,000-100,000 cell/well in progenitor media containing PDGF/FGF and incubated at 37° C. with 5-6% CO2.
4. Media and growth factors are replenished every 48 hr.

Human Culture Compound Treatment:
1. 24 to 48 hr after plating remove the old medium and add compounds in fresh medium (with mitogen)
2. Compound dose response evaluations are performed at 3-6 different concentrations (10 □M, 1 □M, 100 nM, 10 nM, 1 nM, and 0.1 nM)
3. Triplicates wells are run for each compound concentration.
5. Culture the treated cells for 7 d prior to using in experimental assays.

RAT/MOUSE/HUMAN Oligodendrocyte Specific Immunostaining

Following compound exposure, oligodendrocyte-specific antibodies are used to assess ability of compound to accelerate/promote oligodendrocyte differentiation (for example, O4, O1, or myelin basic protein immunoreactivity is over time between compound treated and untreated cultures).
1. Cells are plated onto poly-D-lysine treated 4-well chamber slides at 5×10³ to 20×10³ cells/well and grown as described above. Sequential staining is performed on oligodendrocyte populations with increasing degrees of cellular differentiation, as determined by days ini vitro without PDGF and FGF.
2. Live staining for 30 min at 37° C. is used to detect oligodendrocyte stage specific cell surface marker expression (including A2B5, O4, and O1).
3. Subsequently, cells are fixed with 4% paraformaldehyde, 10 min, room temperature.
4. Fixed staining procedures are used to detect oligodendrocyte stage specific marker expression (including myelin basic protein, MBP).
5. Rinse with PBS.
6. Permeabilize with 0.1% Triton/0.01% NaAz diluted in 1×PBS for 10 min, room temperature.
7. Block with 5-10% goat serum in antibody dilution buffer (0.1% Triton-X 100 and 1% IgG-free bovine serum albumin; also used to dilute antibodies), 15 min, room temperature.
8. Add primary antibody diluted in antibody dilution buffer.
9. Incubate overnight, gently rocking, 4° C.
10. Next day, rinse with PBS 1×5 min, followed by 3×15 min each, room temperature.
11. Incubate with appropriate secondary antibodies, 45 min, room temperature.
12. Cell nuclei are stained with 4,6-diamidino-2-phenylindole (DAPI), 15 min, room temperature.
13. Rinse several times with PBS and evaluate using fluorescent microscopy.
14. The following conditions are compared over time and at different compound doses: PDGF/FGF alone, SFM alone, SFM-IGF1 alone, PDGF/FGF and compound, SFM and compound.

RAT/MOUSE/HUMAN Bromodeoxyuridine (BrdU) Immunostaining

To Confirm that Compounds do not Promote Cell Proliferation.
1. Oligodendrocyte progenitor cells are labeled with 10 □M BrdU for 20 hr and then fixed with either 70% ethanol or 4% paraformaldehyde.
2. The cells are incubated successively with biotinylated mouse anti-BrdU and Streptavidin-Peroxidase, with three intervening washes with PBS.
3. Colormetric visualization of the BrdU immunoreactivity is developed with DAB and total cell numbers are assessed using the counter-stain hematoxylin.
4. BrdU immunopositive cells are counted by two independent observers.

RAT/MOUSE/HUMAN Culture Image Analysis

Fluorescent microscopy is used to quantitate the extent of oligodendrocyte differentiation after compound exposure. This assay demonstrates that selective agonists accelerate/promote oligodendrocytes differentiation.
1. Manual Cell Counting: Four fields are randomly selected for each experimental condition and 500-600 cells are counted in each field. The percentage of MBP (or O4) immunpositive cells (mature process bearing cells with or without myelin sheets) versus DAPI positive cells (total cell number) cells are compared in the control and drug-treated groups.
2. Automated Cell Counting: Fluorescent microscopy was used to quantitate the extent of oligodendrocyte differentiation after compound exposure. Six fields/well were randomly selected to assess the number of differentiating oligodendrocytes among the total population (~8 to 15×10³ cells are counted/well). Immunofluorescence images were obtained using a Zeiss AxioVision digital imaging system, with a Zeiss AxioCam HRc cooled CCD camera connected to the same microscope. All microscopic imaging parameters were set for acquiring images for the analysis of cellular immunofluorescence intensity. The percentage of MBP positive (differentiated) cells versus total cells (DAPI nuclear stained) was compared in the control versus drug-treated groups. Cellular autofluorescence was undetectable under the imaging conditions.

3. Human oligodendrocyte differentiation assay: manually count total number of O4 immunopositive cells/well (bipolar and multipolar).

The results using rat oligodendrocyte cultures are shown in Table 2. As the results show compounds of the instant invention enhance or accelerate rat oligodendrocyte differentiation, as measured by increased myelin basic protein expression compared to untreated controls. This finding suggests compound examples shown in Table 2 would enhance, accelerate, or stimulate oligodendrocyte differentiation and myelin formation in vivo, in the diseased or injured CNS, including MS and other demyelinating disorders.

TABLE 2

Results for Compounds in Primary Rat Oligodendrocyte Differentiation Assay

| Example No. | Fold Increase in Myelin Basic Protein Expression in Oligodendrocyte Differentiation Assay (concentration μM) |
|---|---|
| 10 | 1.5 fold (10) |
| 14 | 1.5 fold (1) |
| 23 | 2 fold (1) |
| 31 | 2 fold (1) |

RAT/MOUSE/HUMAN Quantitative Polymerase Chain Reaction (PCR)

To evaluate compound induced PPAR delta pathway activation and the extent of oligodendrocyte maturation (changes in mRNA levels).

1. Total RNA is extracted from cultured oligodendrocytes using TriZol reagent.
2. Subsequently, mRNA is treated with RNase-free DNase, repurified, and then converted to cDNA template using a RT reaction (Clontech Advantage RT for PCR Kit).
3. PPAR delta pathway member transcript expression is quantitated using Sybr Green PCR Master Mix.
4. The 18S ribosomal RNA primer/probe mix (186 bp product), suspended in Taqman 2×PCR Master Mix is used as an internal control.
5. Quantitative PCR is carried out using real-time Taqman™ technology (Gibson, et al., 1996) with a model 7700 Sequence Detector System (Applied Biosystems, Foster City, Calif.).
6. The results are analyzed using Sequence Detection Systems software version 1.91.

RAT ELISA Assay

To evaluate compound induced PPAR delta pathway activation and the extent of oligodendrocyte maturation (changes in protein levels).

1. Plates are washed with PBS, and then keep on ice. Add 200 μl ice old lysis buffer (Tris 50 mM, pH7.4, MgCl2 2 mM, EDTA 1 mM, β-mercaptoethanol 5 mM, Nonidet P-40 1%, Protease inhibitor cocktail (Roche): 1 tablet/50 ml) to each well.
2. Lyse cells by using pipette to up down and spin plates at 2000 rpm at 4° C. for 5 min. The supernatant is ready to use.
3. Pipet 50 μl of standard, controls and samples to the wells.
4. Add 50 μl of MBP Assay Buffer to each well.
5. Incubate the well, shaking at 500-700 rpm on orbital microplate shaker for 2 hr at room temperature.
6. Add 100 ul of the MBP Antibody-Biotin Conjugate to each well.
7. Incubate the well, shaking at 500-700 rpm on orbital microplate shaker for 1 hr at room temperature.
8. Wash well 5 times with Wash Solution. Blot dry by inverting the plate on absorbent material.
9. Dilute the streptavidin-enzyme conjugate concentrate 1:50 with MBP Elisa Assay buffer. (must be diluted immediately prior to use in the assay).
10. Add 100 μl streptavidin-enzyme conjugate solutions to each well.
11. Incubate the well, shaking at 500-700 rpm on orbital microplate shaker for 30 min at room temperature.
12. Wash well 5 times with the Wash Solution. Blot dry by inverting the plate on absorbent material.
13. Add 100 μl of TMB Chromogen Solution to each well.
14. Incubate the well, shaking at 500-700 rpm on orbital microplate shaker for 10-20 min at room temperature. Avoid exposure to direct sunlight.
15. Add 100 μl of the Stopping Solution to each well.

Read the absorbance of the solution in the wells within 30 min, using a microplate reader set to 450 nM In Vivo Proof of Concept Models Focal Lesions: (Used to Assess Whether Compounds Protect Myelin Integrity or Accelerate/Enhance the Rate of Remyelination.)

1. Rats 7 weeks of age are given free access to food and water and acclimatized for a minimum of 4 days before use in experiments.
2. Prior to surgery each animal is weighed. The rat is then anaesthetized with ketamine (100 mg/ml) in combination with xylazine (20 mg/ml) in a ratio of 1.8:1. The rats are injected with 0.15 ml/180 g body weight i.p. of the anaesthetic solution prior to the surgical procedure. The animal is prepared for surgery using aseptic conditions in accordance with the IACUC guidelines. All surgical instruments will be autoclaved. The hair is clipped between the ears and this region will then be scrubbed with Betadine, flushed with sterile saline and finally wiped with a pre-packaged sterile alcohol swab.
3. For the surgical procedure, the rat is placed on its ventral surface in a small animal stereotaxic instrument designed to hold the head steady. The incisor bar is always set at −3.9 mm, since this has been shown to achieve a flat-skull position for SD rats.
4. An incision is made in the previously shaven skin overlying the skull between the ears.
5. A small area of bone (0.75 mm in diameter) is drilled at the following coordinates AP −1.8, ML −3.1 from lambda.
6. The bone is removed and rats are injected with 2 μl ethidium bromide, lysolecithin, or SIN-1 into the right caudal cerebellar peduncle, DV −7.1 mm, over a 2 min period by means of a Hamilton μl syringe and needle. Alternatively injections are made into the spinal cord, corpus callosum, or cortex.
7. The needle is left in position for the subsequent 2 min.
8. After withdrawal of the needle the incision is sutured.
9. Each rat receives an i.m. injection of 0.003 mg buprenorphine into a hind leg.
10. The rat is placed in a warming cupboard until it regains consciousness. At which time it is returned to its home cage. Do not allow more than 2 rats per cage, as they will pull each other's suture out.
11. Similar procedures are also done using mice.

Rat Experimental Allergic Encephalomyelitis (Rat EAE) Disease Model

Experimental allergic encephalomyelitis (EAE) is a T-cell-mediated autoimmune disease of the nervous system that develops in susceptible animals following sensitization with either whole spinal cord homogenate or a component (myelin basic protein). The EAE rodent model is an appropriate tool for studying the inflammation of the brain and spinal cord observed in MS patients. In rodents, injection of whole spinal cord or spinal cord components such as myelin basic protein induces an autoimmune response based on the activation of T-lymphocytes. Clinical disease typically becomes manifest around day 8-10 after inoculation, observed as a broad spectrum of behavioral anomalies ranging from mild gait disturbances and tail atony to complete paralysis and death. Weight loss typically occurs. In animals that survive, spontaneous recovery occurs, accompanied by variable recovery of most motor function. Depending on the species, allergen, and methodology used, animals tested by the EAE model may experience a single (acute EAE) or several (chronic relapsing EAE) attacks. Several treatment paradigms may be used: the drug or treatment of choice may be administered before immunization, during the nonsymptomatic period or during the clinical disease.

Animals:
Female Lewis rats, 160-220 g (Charles River)

Antigen:
Whole Guinea Pig spinal cord (Harlan Biosciences).
Complete Freund's adjuvant H37 Ra [1 mg,/ml Mycobacterium Tuberculosis H37 Ra] (Difco).

Additional Antigen:
Mycobacterium Tuberculosis (Difco).
Bordetella Pertussis [Heat Killed] (Difco).

Antigen Preparation: (for Approximately 720 Animals):
1. Weigh 5 grams of frozen guinea pig spinal cord.
2. Add 5 g spinal cord to 5 ml 0.9% saline (1 g/ml) in a round bottom centrifuge tube
3. Homogenize on ice with the Tissue-tech until the tissue is completely disrupted (approximately 5 minutes).
4. Add 10 ml Complete Freund's adjuvant H37 Ra supplemented with 200 mg Mycobacterium Tuberculosis (20 mg/ml Complete Freund's adjuvant H37 Ra).
5. Extract homogenate/adjuvant from tube by sucking it into a 10 ml syringe fitted with an 18 gauge emulsifying needle.
6. Emulsify between two 30 ml glass syringes until it becomes difficult to continue passing the material through the needle. (Approximately 5 minutes {there must be no separation between the oil phase and the aqueous phase}).
7. Use immediately or keep on ice until needed (not more than 30 min) (do not freeze).

Protocol

1. Female Lewis rats (Charles River) are given free access to food and water and should be acclimated a minimum of 3 days before use in experiments.
2. Rats weighing 160 and 220 grams are initially induced with 5% isoflurane (Aerrane, Fort Dodge), 30% $O_2$, 70% $N_2O$ for 2-5 minutes.
3. The rat is then placed onto a circulating water heating blanket (Gaymar) (dorsal surface up) and into the nose cone for spontaneous respiration of anesthetic gases. The isoflurane is reduced to 2%.
4. Two subcutaneous injections (0.1 ml each) of either antigen or normal saline are made into ventral surface of the hind paws.
5. The animals are removed from the nose cone, weighed and numbered.
6. The rats are allowed to awake from anesthesia and are placed into individual cages.
7. The animals are observed daily for signs of EAE induction (see criteria below)

| | |
|---|---|
| STAGE: 0 | NORMAL |
| STAGE 1 | Abnormal gate and tail atony |
| STAGE 2 | Mild but definite weakness of one or both hind legs |
| STAGE: 3 | Severe weakness of one or both hind legs or mild ataxia |
| STAGE: 4 | Severe paraparesis and minimal hind leg movement |
| STAGE: 5 | No hind leg movement and paraplegia |
| STAGE: 6 | Moribund state with no spontaneous movement and impaired respiration. Increasing degree of front leg involvement and urinary and fecal incontinence may also occur |
| STAGE: 7 | DEATH |

Treatment is begun on day 10 after immunization. Since the disease symptoms in this model typically appear 10-11 days after inoculation, this time point may be considered to represent the initial phase of an acute episode of MS. It is judged that this delay of the start of treatment mimics the clinical situation more closely than the traditionally used protocols where drugs are administered at the time of, or even before, inoculation (Teitelbaum D. et al., Proc Natl Acad Sci USA 1999; 96: 3842-3847 and Brod S. A., et al., Ann Neurol 2000; 47: 127-131).

This invention is further illustrated by the following examples of compounds used herein which are provided for illustration purposes and in no way limit the scope of the present invention.

SYNTHETIC EXAMPLES

General

Commercial reagents and solvents were used as received. $^1$H NMR spectra were recorded on a Varian MercuryPlus-300 (300 MHz) or Varian Unity Inova (400 MHz) spectrometer as indicated. Proton chemical shifts are reported in □ ppm relative to internal tetramethylsilane (0.0 ppm). MS (LC-MS) data is obtained using a Micromass LCT time of flight mass spectrometer with electrospray ionization and 5 min data acquisition time for m/z 100 to 1000. LC (LC-MS) is performed using a Hypersil C18 column (4.6×50 mm, 3.5□ with mobile phase of 0.1% TFA in $H_2O$ (A) and 0.1% TFA in ACN (B) and a gradient of 5% to 100% B over 3 min followed by 2 min at 100% B. Alternatively, a Platform LC-MS with electrospray source may be used with a HP1100 LC system running at 2.0 ml/min, 200 □L/min split to the ESI source with inline HP1100 DAD detection and SEDEX ELS detection. A Luna C18(2) column (30×4.6 mm 3□ is used with a gradient of 5% to 95% B over 4.5 min with mobile phase of 0.1% formic acid in $H_2O$ and 0.1% formic acid in ACN (B). HPLC purification is performed on a Varian ProStar system using a reversed-phase C18 column with a linear gradient of ACN/$H_2O$ containing 0.1% trifluoroacetic acid. Microwave syntheses were performed using a Personal Chemistry Smithcreator microwave reaction system using 2 or 5 mL reactor vessels.

Example 1

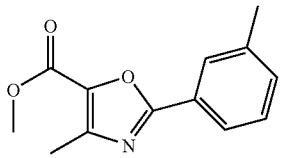

Intermediate:
4-Methyl-2-m-tolyl-oxazole-5-carboxylic acid
methyl ester

Heat to 120° C. a neat mixture of methyl 2-chloroacetoacetate (914 mL, 7.5 mmol) and 3-methyl-benzamide (676 mg, 5 mmol) and stir at this temperature for 12 hrs. Cool the reaction mixture to room temperature and dilute it with ethyl acetate, wash with saturated sodium bicarbonate solution (3 times), water (twice) and brine, Dry the organic extract over MgSO4 and concentrate. Purify the resulting residue by flash chromatography (elute with 10% ethyl acetate in heptane) to give the title compound as a yellow oil (492 mg).

Example 2

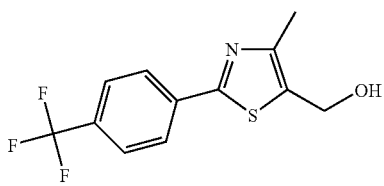

Intermediate: [4-Methyl-2-(4-trifluoromethyl-phenyl)-thiazol-5-yl]-methanol

Cool (0° C.) a solution of lithium aluminum hydride (10 mL, 1M in THF) and add a solution of 4-methyl-2-(4-trifluoromethyl-phenyl)-thiazole-5-carboxylic acid (Commercially available, 2.87 g, 10 mmol) in THF (20 mL). On complete addition, remove the cold bath and stir for 3.5 hrs. Cool this solution to 5° C., and then add water (0.25 mL), dropwise, followed by NaOH solution (0.25 mL, 5M in water) and water (0.5 mL). Dilute the resulting mixture with ethyl acetate and then filter through a pad of celite. Wash the solids with dichloromethane and then concentrate the combined filtrates under reduced pressure to give the title compound as a yellow solid (2.59 g).

MS (ESI), m/z 274 (M+H); H1 NMR (CDCl$_3$), δ 1.87 (bs, 1H), 2.49 (s, 3H), 4.86 (s, 2H), 7.67 (d, J=8 Hz, 2H), 8.02 (d, J=8 Hz, 2H).

Example 3

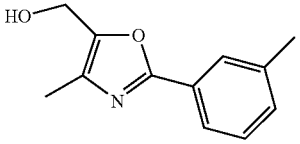

Intermediate:
[4-Methyl-2-m-tolyl-oxazol-5-yl]-methanol

Follow the procedure of Example 2, but use the compound of Example 1 as the starting material to obtain the title compound.

MS (ESI), m/z 204 (M+H); H1 NMR (CDCl$_3$), δ 2.25 (s, 3H), 2.40 (t, J=7 Hz, 1H), 2.42 (s, 3H), 4.70 (d, J=7 Hz, 2H), 7.25-7.36 (m, 2H), 7.75-7.85 (m, 2H).

Example 4

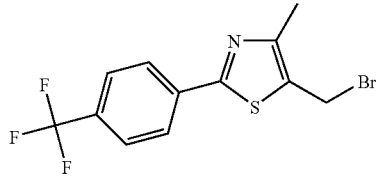

Intermediate: 5-Bromomethyl-4-methyl-2-(4-trifluoromethyl-phenyl)-thiazole

Cool (10° C.) a solution of [4-methyl-2-(4-trifluoromethyl-phenyl)-thiazol-5-yl]-methanol (Example 2, 753 mg, 3 mmol) in THF (12 mL) add triphenylphosphine (864 mg, 3.3 mmol) followed by freshly recrystallized N-bromosuccinimide (587 mg, 3.3 mmol). On complete addition, remove the cold bath and stir continuously for 45 min. Concentrate the resulting mixture under vacuum and purify the residue by flash chromatography (elute with 10% ethyl acetate/10% dichloromethane in heptane) to give the title compound as an orange solid (846 mg).

MS (ESI), m/z 336, 338 (M+H); H1 NMR (CDCl$_3$) δ 2.48 (s, 3H), 4.72 (s, 2H), 7.69 (d, J=8 Hz, 2H), 8.01 (d, J=8 Hz, 2H).

Example 5

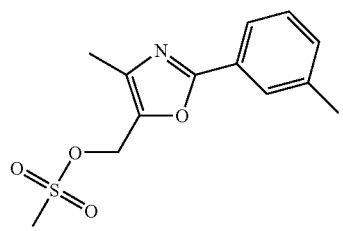

Intermediate: Methanesulfonic acid
[2-(3-methyl-phenyl)-4-methyl oxazol-5-yl]-methyl
ester Cool (0° C.) a solution of [2-(3-methyl-phenyl)-4-methyl oxazol-5-yl]-methanol (Example 3, 756 mg, 4 mmol) in dichloromethane (16 mL) and add, sequentially, DMAP (51 mg, 0.4 mmol), triethylamine (552 μL, 4 mmol) and methanesulfonyl chloride (323 μL, 4.2 mmol). Stir the resulting solution for 5 min., remove the cooling bath and stir for 25 min. Dilute this solution with ether, wash with hydrochloric acid (5 mL, 2M), brine, dry over MgSO$_4$ and concentrate to give the title compound (743 mg).

Example 6

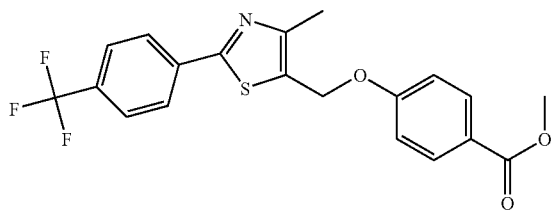

Intermediate: 4-[4-Methyl-2-(4-trifluoromethyl-phenyl)-thiazol-5-ylmethoxy]-benzoic acid methyl ester To a mixture of 4-hydroxy-benzoic acid methyl ester (152 mg, 1 mmol) and potassium carbonate (152 mg, 1.1 mmol) add acetonitrile (4 mL). To this mixture add 5-bromomethyl-4-methyl-2-(4-trifluoromethyl-phenyl)-thiazole (Example 4, 314 mg, 1 mmol). Warm the resulting reaction mixture to 60° C., and stir at this temperature for 5 hrs. Cool the mixture to room temperature, dilute with ethyl acetate, wash with water, then brine, dry over MgSO$_4$, filter and concentrate to give the title compound as a white solid (364 mg).

MS (ESI), m/z 408 (M+H); H1 NMR (CDCl$_3$), δ 2.53 (s, 3H), 3.90 (s, 3H), 4.52 (s, 2H), 7.00 (d, J=9 Hz, 2H), 7.68 (d, J=8 Hz, 2H), 8.02 (m, 4H).

Example 7

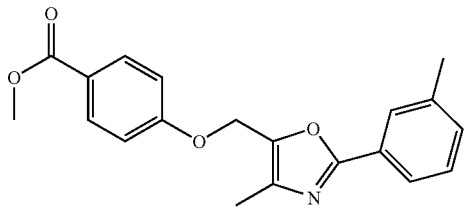

Intermediate: 4-(4-Methyl-2-m-tolyl-oxazol-5-ylmethoxy)-benzoic acid methyl ester Follow the procedure of Example 6, but use the compound of Example 5 as the starting material to obtain the title compound.

MS (ESI), m/z 338 (M+H); H1 NMR (CDCL$_3$), δ 2.30 (s, 3H), 2.41 (s, 3H), 3.90 (s, 3H), 5.11 (s, 2H), 7.03 (d, J=9 Hz, 2H), 7.25 (m, 1H), 7.33 (t, J=8 Hz, 1H), 7.81 (d, J=8 Hz, 1H), 7.87 (bs, 1H), 8.02 (d, J=9 Hz, 2H).

Example 8

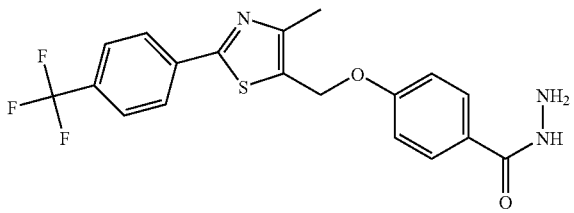

Intermediate: 4-[4-Methyl-2-(4-trifluoromethyl-phenyl)-thiazol-5-ylmethoxy]-benzoic acid hydrazide To a suspension of 4-[4-methyl-2-(4-trifluoromethyl-phenyl)-thiazol-5-ylmethoxy]-benzoic acid methyl ester (Example 6, 364 mg, 1 mmol) in methanol (10 mL) add anhydrous hydrazine (128 ml, 4 mmol). Warm the resulting mixture to 60° C. and stir at this temperature for 18 hrs. Cool the resulting solution to room temperature, and add 3 drops of water. Concentrate the solution under vacuum and purify the residue by flash chromatography (elute with 5% methanol in dichloromethane) to give the title compound (271 mg).

MS (ESI), m/z 408 (M+H); H1 NMR (DMSO), δ 2.51 (s, 3H), 4.4 (bs, 2H), 5.42 (s, 2H), 7.10 (d, J=9 Hz, 2H), 7.82 (d, J=9 Hz, 2H), 7.85 (d, J=8 Hz, 2H), 8.12 (d, J=8 Hz, 2H), 9.63 (bs, 1H).

Example 9

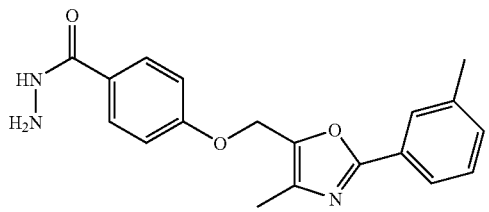

Intermediate: 4-(4-Methyl-2-m-tolyl-oxazol-5-ylmethoxy)-benzoic acid hydrazide

Follow the procedure of Example 8, but use the compound of Example 7 as the starting material to obtain the title compound.

MS (ESI), m/z 338 (M+H); H1 NMR (DMSO), δ 2.24 (s, 3H), 2.38 (s, 3H), 4.43 (bs, 2H), 5.26 (s, 2H), 7.11 (d, J=9 Hz, 2H), 7.34 (d, J=8 Hz, 1H), 7.41 (t, J=8 Hz, 1H), 7.74-7.83 (m, 4H), 9.63 (bs, 1H).

Example 10

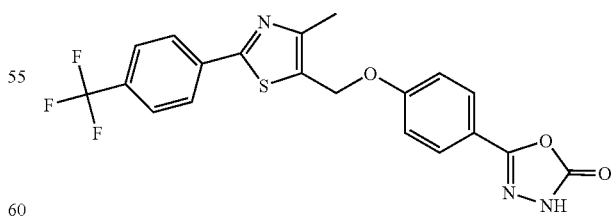

5-{4-[4-Methyl-2-(4-trifluoromethyl-phenyl)-thiazol-5-ylmethoxy]-phenyl}-3H-[1,3,4]oxadiazol-2-one To a suspension of 4-[4-methyl-2-(4-trifluoromethyl-phenyl)-thiazol-5-ylmethoxy]-benzoic acid hydrazide (Example 8, 271 mg, 0.74 mmol) in dichloromethane (7 mL) add phenylchloroformate (94 μL, 0.75 mmol) followed by pyridine (132 μL, 1.63 mmol). Stir the resulting mixture at room temperature until all the starting material is consumed (by TLC analysis). Concentrate the mixture, and then take the residue up in acetonitrile (10 mL). To this mixture, add DBU (220 μL, 1.5 mmol). Seal the resulting solution; warm it to 180° C. in a Personal Chemistry™ microwave oven and stir at this temperature for 15 min. Cool the reaction to room temperature, dilute with ethyl acetate, wash with 1 M HCl solution (or saturated $NaH_2PO_4$ solution) dry over $MgSO_4$ and concentrate. Triturate the resulting residue with dichloromethane several times to give the title compound as a tan solid (69 mg).

MS (ESI), m/z 365 (M+H); H1 NMR (DMSO), δ 2.51 (s, 3H), 4.4 (bs, 2H), 5.42 (s, 2H), 7.10 (d, J=9 Hz, 2H), 7.82 (d, J=9 Hz, 2H), 7.85 (d, J=8 Hz, 2H), 8.12 (d, J=8 Hz, 2H), 9.63 (bs, 1H).

Example 11

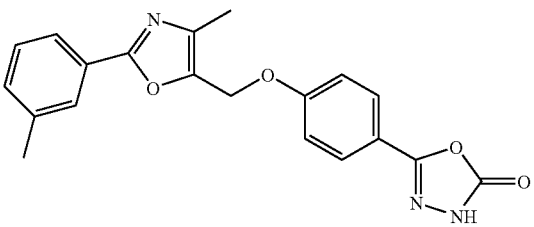

5-[4-(4-Methyl-2-m-tolyl-oxazol-5-ylmethoxy)-phenyl]-3H-[1,3,4]oxadiazol-2-one

Follow the procedure of Example 10, but use the compound of Example 9 as the starting material to obtain the title compound.

MS (ESI), m/z 364 (M+H); H1 NMR (DMSO), δ 2.25 (s, 3H), 2.38 (s, 3H), 5.30 (s, 2H), 7.23 (d, J=9 Hz, 2H), 7.34 (d, J=8 Hz, 1H), 7.41 (t, J=8 Hz, 1H), 7.75-7.79 (m, 4H), 12.44 (bs, 1H).

Example 12

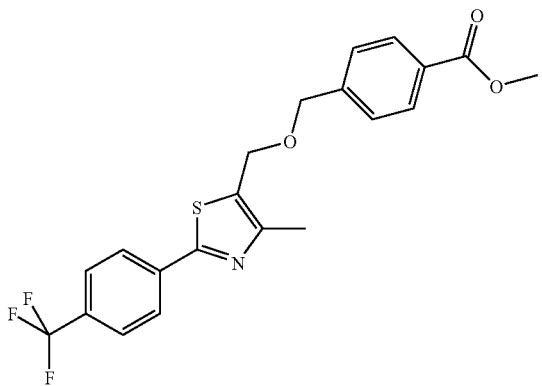

Intermediate: 4-([4-Methyl-2-(4-trifluoromethyl-phenyl)-thiazol-5-yl)-methoxymethyl]-benzoic acid methyl ester Cool (−5° C.) a suspension of NaH (84 mg, 60% dispersion in mineral oil, 2.05 mmol) in THF (4 mL) and add a solution comprised of 2-([4-methyl-2-(4-trifluoromethyl-phenyl)-thiazol-5-yl)-methanol (546 mg, 2 mmol) and 4-bromomethyl-benzoic acid methyl ester (458 mg, 2 mmol) in THF (5 mL). Stir the resulting mixture for 5 min then the remove the cold bath and stir for an additional 3 hr. Quench the reaction with 1M HCl solution, dilute with ethyl acetate, wash with brine and dry over Mg $SO_4$. Concentrate this solution under vacuum and purify the residue by flash chromatography (eluting with 20% ethyl acetate in heptane) to give the product (377 mg) as a white solid.

MS (ESI), m/z 422 (M+H); H1 NMR ($CDCl_3$), δ 2.44 (s, 3H), 3.92 (s, 3H), 4.64 (s, 2H), 4.71 (s, 2H), 7.42 (d, J=8 Hz, 2H), 7.66 (d, J=8 Hz, 2H), 8.00 (m, 4H).

Example 13

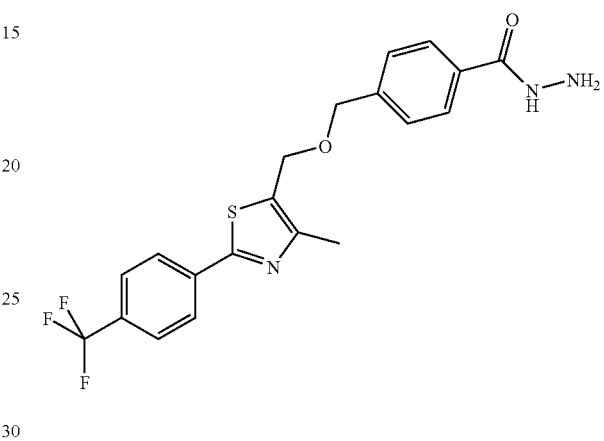

Intermediate: 4-([4-Methyl-2-(4-trifluoromethyl-phenyl)-thiazol-5-yl)-methoxymethyl]-benzoic acid hydrazide Follow the procedure of Example 8, but use the compound of Example 12 as the starting material to obtain the title compound.

MS (ESI), m/z 422 (M+H); H1 NMR ($CDCl_3$), δ 2.44 (s, 3H), 4.09 (bs, 2H), 4.63 (s, 2H), 4.71 (s, 2H), 7.30 (bs, 1H), 7.44 (d, J=8 Hz, 2H), 7.66 (d, J=8 Hz, 2H), 7.73 (d, J=8 Hz, 2H), 8.00 (d, J=8 Hz, 2H).

Example 14

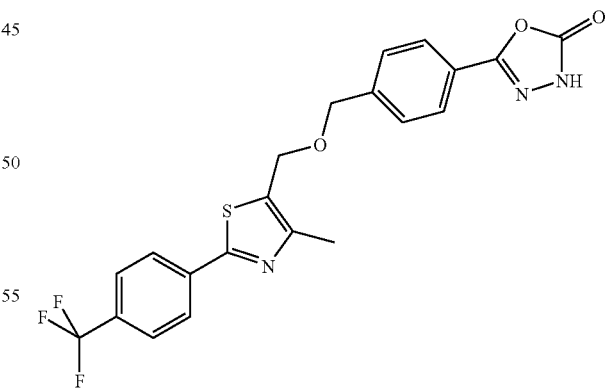

5-{4-[4-Methyl-2-(4-trifluoromethyl-phenyl)-thiazol-5-yl)-methoxymethyl]-phenyl}-3H-[1,3,4]oxadiazol-2-one Follow the procedure of Example 10, but use the compound of Example 13 as the starting, material to obtain the title compound.

MS (ESI), m/z 448 (M+H); H1 NMR (DMSO), δ 2.40 (s, 3H), 4.65 (s, 2H), 4.78 (s, 2H), 7.50 (d, J=8 Hz, 2H), 7.78 (d, J=8 Hz, 2H), 7.82 (d, J=8 Hz, 2H), 8.10 (d, J=8 Hz, 2H), 12.54 (bs, 1H).

Example 15

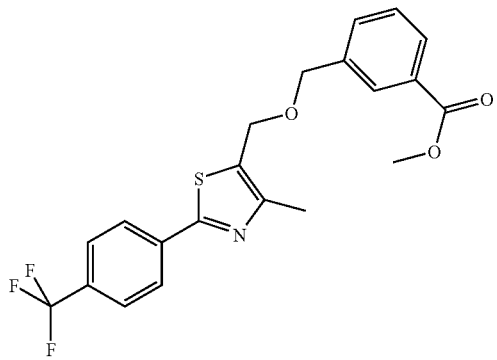

Intermediate: 4-([3-Methyl-2-(4-trifluoromethyl-phenyl)-thiazol-5-yl)-methoxymethyl]-benzoic acid methyl ester Cool (0° C.) a solution of 2-([4-methyl-2-(4-trifluoromethyl-phenyl)-thiazol-5-yl)-methanol (450 mg, 1.64 mmol) in THF and add NaH (70 mg, 50% dispersion in mineral oil, 1.75 mmol). Stir the resulting mixture for 5 min. Remove the cold bath and continue stirring for 1 hr. To this mixture add 3-(bromomethyl)-benzoic acid methyl ester (450 mg, 1.95 mmol). Stir the resulting mixture for 3 hr then quench the reaction with sat. NH$_4$Cl solution. Dilute the mixture with ether, wash with brine, dry over MgSO$_4$ and concentrate under vacuum. Purify the residue by flash chromatography (eluting with 30% ethyl acetate in heptane) to give the title compound (181 mg) as an oil.

MS (ESI), m/z 422 (M+H); H1 NMR (CDCl$_3$), δ 2.44 (s, 3H), 3.92 (s, 3H), 4.63 (s, 2H), 4.71 (s, 2H), 7.44 (t, J=8 Hz, 1H), 7.56 (d, J=8 Hz, 1H), 7.66 (d, J=8 Hz, 2H)), 7.00 (m, 4H).

Example 16

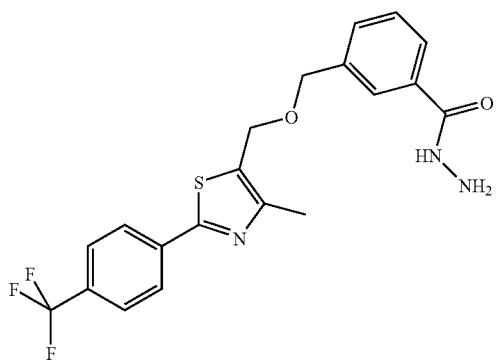

Intermediate: 4-([3-Methyl-2-(4-trifluoromethyl-phenyl)-thiazol-5-yl)-methoxymethyl]-benzoic acid hydrazide Follow the procedure of Example 8, but use the compound of Example 15 as the starting material to obtain the title compound.

Example 17

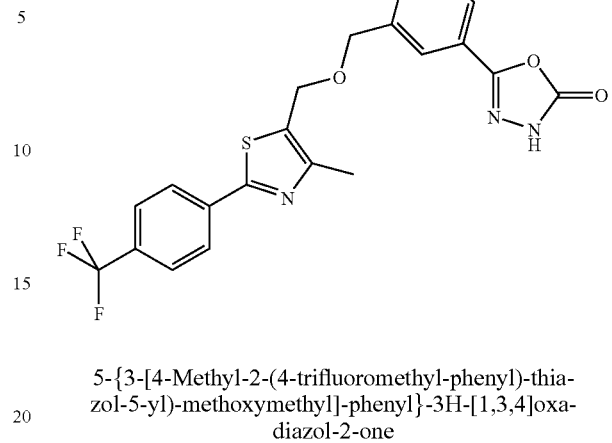

5-{3-[4-Methyl-2-(4-trifluoromethyl-phenyl)-thiazol-5-yl)-methoxymethyl]-phenyl}-3H-[1,3,4]oxadiazol-2-one Follow the procedure of Example 10, but use the compound of Example 16 as the starting material to obtain the title compound.

MS (ESI), m/z 448 (M+H); H1 NMR (DMSO), δ 2.40 (s, 3H), 4.65 (s, 2H), 4.79 (s, 2H), 7.53 (m, 2H), 7.72 (m, 1H), 7.77 (s, 1H), 7.82 (d, J=8 Hz, 2H), 8.10 (d, J=8 Hz, 2H), 12.5 (bs, 1H).

Example 18

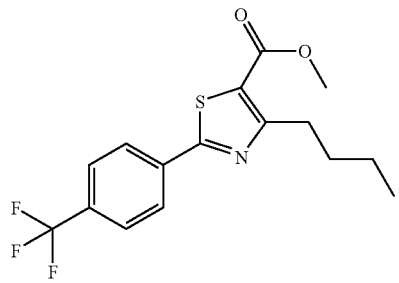

Intermediate: 4-Butyl-2-(4-trifluoromethyl-phenyl)-thiazol-5-carboxylic acid methyl ester To a solution of 3-oxo-heptanoic acid methyl ester (5.0 g, 31.6 mmol) in dry dichloromethane (80 mL) add sulfurylchloride (2.82 mL). Stir the reaction mixture at room temperature for 30 minutes then add water (20 mL) and the reaction mixture extracted five times with portions of 30 mL of dichloromethane. Wash the combined organic extracts with water, saturated aqueous solution of NaHCO$_3$ and brine and then dry over MgSO$_4$. Remove the solvent under reduced pressure to give 2-chloro-3-oxo-heptanoic acid methyl ester (6.0 g), which was used in the next step without further purification. To a solution of 2-chloro-3-oxo-heptanoic acid methyl ester (6.0 g, 31.1 mmol) in ethanol (50 mL) add 4-(trifluoromethyl) thiobenzamide (6.4 g, 31.2 mmol). Heat the reaction mixture to reflux overnight. Remove the solvent under reduced pressure and purify the residue by chromatography on silica gel (eluting with a gradient of n-heptane:ethyl acetate (100:1 to 60:1)) to give 4-butyl-2-(4-trifluoromethyl-phenyl)-thiazol-5-carboxylic acid methyl ester (7.4 g) as a yellow oil.

MS (ESI), m/z 344 (M+H).

Example 19

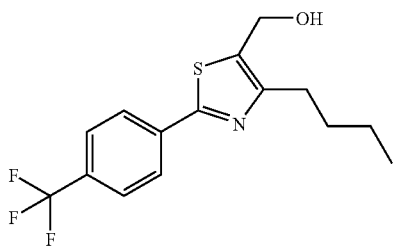

Intermediate: [4-Butyl-2-(4-trifluoromethyl-phenyl)-thiazole-5-yl]-methanol

To a solution of lithium aluminium hydride (1.2 g) in dry tetrahydrofuran (100 mL) add 4-butyl-2-(4-trifluormethyl-phenyl)-thiazol-5-carboxylic acid methyl ester (5.3 g, 15.4 mmol) dissolved in tetrahydrofuran (100 mL). Stir the reaction mixture at room temperature over a period of one hour. Add a saturated aqueous solution of ammonium chloride (50 mL) and then a 1 molar aqueous solution of hydrochloric acid (50 mL). Extract the reaction mixture five times with portions of 60 ml of ethyl acetate. Dry the combined extracts with MgSO$_4$ and remove the solvent under reduced pressure to provide [4-butyl-2-(4-trifluoromethyl-phenyl)-thiazole-5-yl]-methanol (4.6 g) as a yellow oil, which solidified upon standing at room temperature.

MS (ESI), m/z 316 (M+H); H1 NMR (DMSO-d6), δ 0.91 (t, J=7.0 Hz, 3H), 1.35 (m, 2H), 1.64 (m, 2H), 2.70 (m, 2H), 4,68 (bm, 2H), 5.63 (bm, 1H), 7.83 (bd, J=8.5 Hz, 2H), 8.09 (bd, J=8.5 Hz, 2H).

Example 20

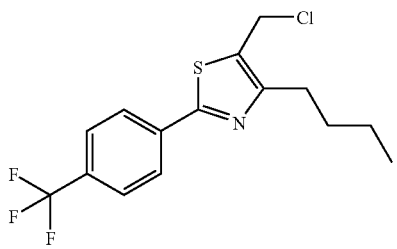

Intermediate: 4-Butyl-5-chloromethyl-2-(4-trifluoromethyl-phenyl)-thiazole

To a solution of [4-butyl-2-(4-trifluoromethyl-phenyl)-thiazole-5-yl]-methanol (1.0 g, 3.1 mmol) in dichloromethane (50 mL) add triethylamine (0.88 mL) and methanesulfonyl chloride (0.39 mL). Stir the reaction mixture at room temperature for a period of three hours then add dichloromethane (100 mL). Wash the reaction mixture with a saturated aqueous solution of NaHCO$_3$ (50 mL), water and brine. Dry the organic layer over MgSO$_4$ and remove the solvent under reduced pressure to give 4-butyl-5-chloromethyl-2-(4-trifluoromethyl-phenyl)-thiazole (1.0 g) as a yellow oil.

MS (ESI), m/z 334 (M+H); H1 NMR (DMSO-d6), δ 0.92 (t, J=7.5 Hz, 3H), 1.37 (m, 2H), 1.68 (m, 2H), 2.80 (m, 2H), 5.14 (s, 2H), 7.86 (bd, J=8.5 Hz, 2H), 8.12 (bd, J=8.5 Hz, 2H).

Example 21

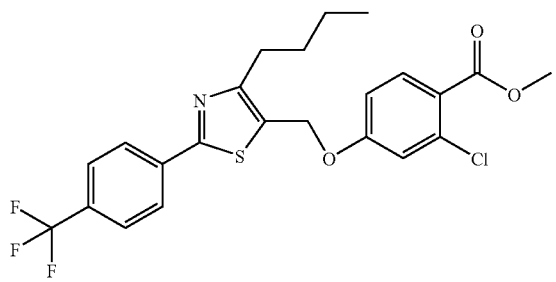

Intermediate: 4-[4-Butyl-2-(4-trifluoromethyl-phenyl)-thiazol-5-ylmethoxy]-2-chloro-benzoic acid methyl ester To an ice-cold solution of [4-butyl-2-(4-trifluoromethyl-phenyl)-thiazole-5-yl]-methanol (1.0 g, 3.17 mmol), 2-chloro-4-hydroxy-benzoic acid methyl ester (592 mg, 3.17 mmol) and triphenylphosphine (832 mg, 3.17 mmol) in dichloromethane add diethyl azodicarboxylate (0.567 mL, 3.17 mmol). Stir the reaction mixture for 2 hours while allowing it to warm to room temperature. Remove the solvent under reduced pressure and purify the residue by flash chromatography on silica gel to give 4-[4-butyl-2-(4-trifluoromethyl-phenyl)-thiazol-5-ylmethoxy]-2-chloro-benzoic acid methyl ester (600 mg).

MS (ESI), m/z 484 (M+H).

Example 22

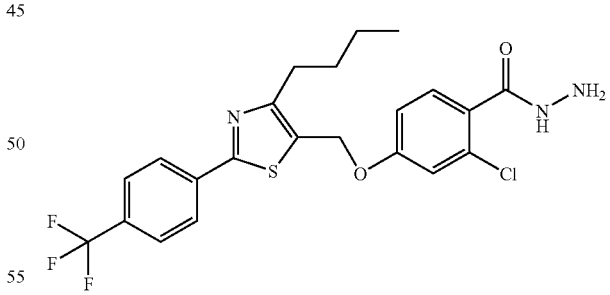

Intermediate: 4-[4-Butyl-2-(4-trifluoromethyl-phenyl)-thiazol-5-ylmethoxy]-2-chloro-benzoic acid hydrazide Follow the procedure of Example 8, but use the compound of Example 21 as the starting material to obtain the title compound.

MS (ESI), m/z 484 (M+H).

Example 23

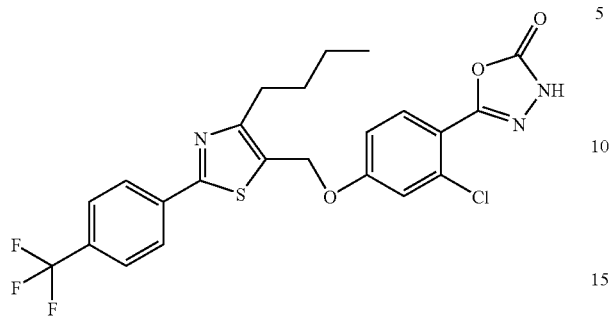

5-{4-[4-Butyl-2-(4-trifluoromethyl-phenyl)-thiazol-5-ylmethoxy]-2-chloro-phenyl}-3H-1,3,4]oxadiazol-2-one Follow the procedure of Example 10, but use the compound of Example 22 as the starting material to obtain the title compound.

MS (ESI), m/z 510 (M+H); H1 NMR (DMSO-d6), δ 0.91 (t, 3H), 1.37 (m, 2H), 1.68 (m, 2H), 2.83 (t, 2H), 5.50 (s, 2H), 7.19 (dd, J=9, 2.5 Hz, 1H), 7.40 (d, J=2.4 Hz, 1H), 7.77 (d, J=8.6 Hz, 1H), 7.86 (d, J=8.0 Hz, 2H), 8.13 (d, J=8.3 Hz, 2H), 12.64 (bs, 1H).

Example 24

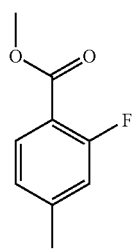

Intermediate: 2-Fluoro-4-methyl-benzoic acid methyl ester

To a solution of 2-fluoro-4-methyl-benzoic acid (1.1 g, 7.13 mmol) in methanol (20 mL) add thionyl chloride (1.02 g, 8.56 mmol). Stir the resulting mixture overnight then concentrate under vacuum to give the title compound (1.2 g) as a white solid.

MS (ESI), m/z 169 (M+H); H1 NMR (DMSO-d6), δ 2.37 (s, 3H), 3.83 (s, 3H), 7.12-7.21 (m, 2H), 7.79 (t, J=8.0 Hz, 1H).

Example 25

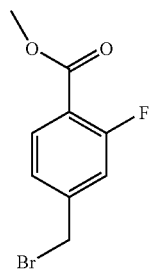

Intermediate: 4-Bromomethyl-2-Fluoro-benzoic acid methyl ester

To a solution of 2-fluoro-4-methyl-benzoic acid methyl ester (1.12 g, 6.66 mmol) in carbon tetrachloride (12 mL) add N-bromosuccinimide (1.18 g, 6.66 mmol) and benzoyl peroxide (10 mg). Heat the resulting mixture to 60° C. for 15 hours then concentrate under vacuum to half and filter. Concentrate the filtrate under vacuum and purify the resulting crude product by flash chromatography on silica gel (eluting with 5/1 heptane/ethyl acetate) to give the title compound (1.35 g) as a white solid.

MS (ESI), m/z 247 (M+H); H1 NMR (DMSO-d6), δ 3.85 (s, 3H), 4.73 (s, 2H), 7.37-7.48 (m, 2H), 7.88 (t, J=8.0 Hz, 1H).

Example 26

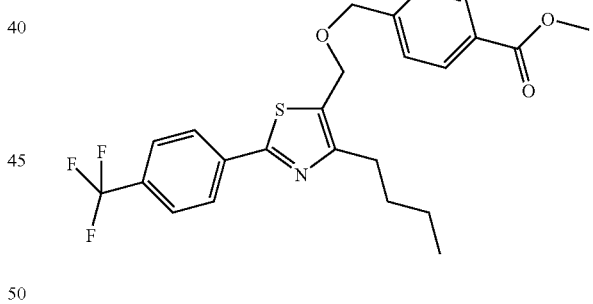

Intermediate: 4-[4-Butyl-2-(4-trifluoromethyl-phenyl)-thiazol-5-ylmethoxymethyl]-2-fluoro-benzoic acid methyl ester To a solution of [4-butyl-2-(4-trifluoromethyl-phenyl)-thiazole-5-yl]-methanol (1.02 g, 3.24 mmol) in anhydrous DMF (150 mL) add cesium carbonate (2.7 g, 8.10 mmol) and 4-bromomethyl-2-fluoro-benzoic acid methyl ester (0.8 g, 3.24 mmol). Stir the resulting mixture overnight then pour into a 1M aqueous solution of potassium hydrogenophosphate and extracted three times with diisopropyl ether. Wash the combined extracts with water, dry over MgSO4, filter and concentrate under vacuum. Purify the residue by flash chromatography on silica gel (eluting with a gradient of heptane/ethyl acetate) to give the title compound (0.3 g) as a yellow solid.

MS (ESI), m/z 482 (M+H); H1 NMR (DMSO-d6), δ 0.89 (t, J=7.5 Hz, 3H), 1.33 (m, 2H), 1.65 (m, 2H), 2.72 (m, 2H), 3.86 (s, 3H), 4.67 (s, 2H), 4.80 (s, 2H), 7.28-7.34 (m, 2H), 7.86 (bd, J=8.5 Hz, 2H), 7.90 (t, J=8.0 Hz, 1H), 8.11 (bd, J=8.5 Hz, 2H).

Example 27

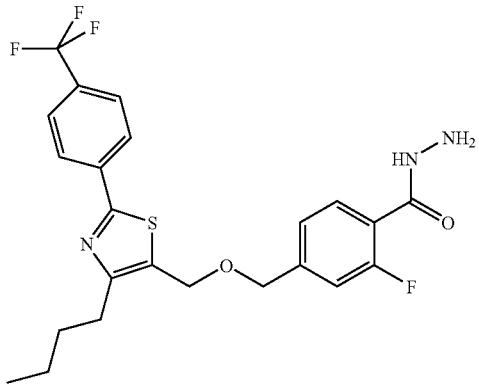

Intermediate: 4-[4-Butyl-2-(4-trifluoromethyl-phenyl)-thiazol-5-ylmethoxymethyl]-2-fluoro-benzoic acid hydrazide Follow the procedure of Example 8, but use the compound of Example 26 as the starting material to obtain the title compound.

MS (ESI), m/z 482 (M+H); H1 NMR (DMSO-d6), δ 0.90 (t, J=7.5 Hz, 3H), 1.33 (m, 2H), 1.65 (m, 2H), 2.72 (m, 2H), 4.53 (bs, 2H), 4.62 (s, 2H), 4.79 (s, 2H), 7.20-7.29 (m, 2H), 7.57 (bt, J=8.0 Hz, 1H), 7.84 (bd, J=8.5 Hz, 2H), 8.12 (bd, J=8.5 Hz, 2H), 9.51 (m, 1H).

Example 28

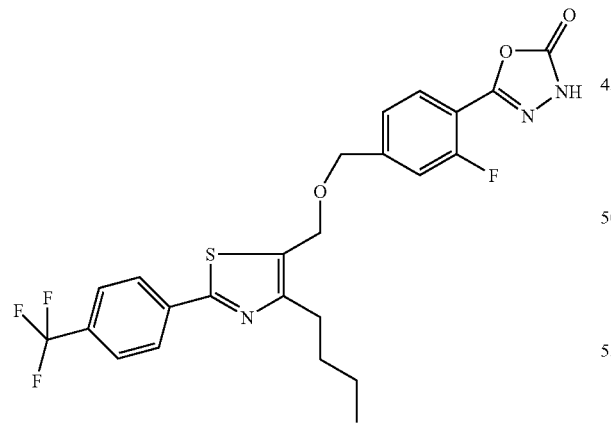

5-{4-[4-Butyl-2-(4-trifluoromethyl-phenyl)-thiazol-5-ylmethoxymethyl]-2-fluoro-phenyl}-3H-[1,3,4]oxadiazol-2-one Follow the procedure of Example 10, but use the compound of Example 27 as the starting material to obtain the title compound.

MS (ESI), m/z 508 (M+H); H1 NMR (DMSO-d6), δ 0.89 (t, J=7.5 Hz, 3H), 1.33 (m, 2H), 1.65 (m, 2H), 2.73 (m, 2H), 4.68 (s, 2H), 4.81 (s, 2H), 7.33-7.40 (m, 2H), 7.80 (t, J=8.0 Hz, 1H), 7.85 (bd, J=8.5 Hz, 2H), 8.12 (bd, J=8.5 Hz, 2H), 12.70 (bm, 1H).

Example 29

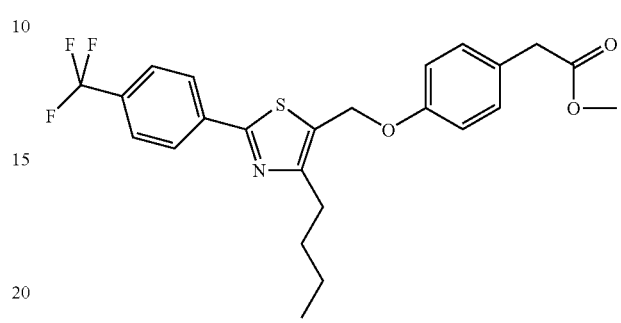

Intermediate: {4-[4-Butyl-2-(4-trifluoromethyl-phenyl)-thiazol-5-ylmethoxy]-phenyl}-acetic acid methyl ester To a solution of 4-butyl-5-chloromethyl-2-(4-trifluoromethyl-phenyl)-thiazole (278 mg, 0.83 mmol) in anhydrous DMF (5 mL) add cesium carbonate (297 mg, 1.66 mmol) and methyl 4-hydroxyphenylacetate (200 mg, 1.20 mmol). Stir the resulting mixture overnight then pour into water and extract twice with ethyl acetate. Wash the combined extracts with water, dry over MgSO$_4$, filter and concentrate under vacuum to give the title compound (290 mg) as a yellowish solid.

MS (ESI), m/z 508 (M+H); H1 NMR (DMSO-d6), δ 0.90 (t, J=7.5 Hz, 3H), 1.36 (m, 2H), 1.67 (m, 2H), 2.80 (m, 2H), 3.60 (s, 3H), 3.61 (s, 2H), 5.33 (s, 2H), 7.00 (bd, J=8.5 Hz, 2H), 7.21 (bd, J=8.5 Hz, 2H), 7.84 (bd, J=8.5 Hz, 2H), 8.12 (bd, J=8.5 Hz, 2H).

Example 30

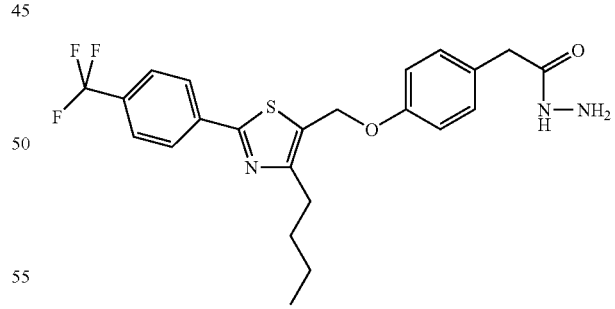

Intermediate: {4-[4-Butyl-2-(4-trifluoromethyl-phenyl)-thiazol-5-ylmethoxy]-phenyl}-acetic acid hydrazide Follow the procedure of Example 8, but use the compound of Example 29 as the starting material to obtain the title compound.

MS (ESI), m/z 464 (M+H); H1 NMR (DMSO-d6), δ 0.91 (t, J=7.5 Hz, 3H), 1.36 (m, 2H), 1.67 (m, 2H), 2.80 (m, 2H), 3.28 (s, 2H), 4.17 (bd, J=4.0 Hz, 2H), 5.32 (s, 2H), 6.97 (bd, J=8.5 Hz, 2H), 7.19 (bd, J=8.5 Hz, 2H), 7.84 (bd, J=8.5 Hz, 2H), 8.12 (bd, J=8.5 Hz, 2H), 9.13 (bt, J=4.0 Hz, 1H).

Example 31

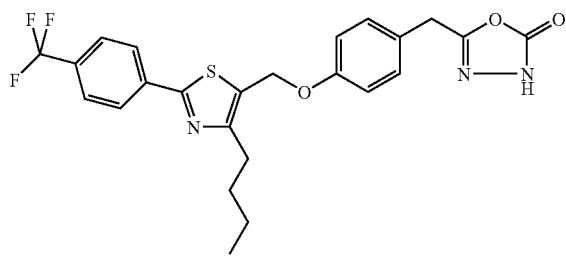

5-{4-[4-Butyl-2-(4-trifluoromethyl-phenyl)-thiazol-5-ylmethoxy]-benzyl}-3H-[1,3,4]oxadiazol-2-one Follow the procedure of Example 10, but use the compound of Example 30 as the starting material to obtain the title compound.

MS (ESI), m/z 490 (M+H); H1 NMR (DMSO-d6), δ 0.90 (t, J=7.5 Hz, 3H), 1.36 (m, 2H), 1.68 (m, 2H), 2.80 (m, 2H), 3.87 (s, 2H), 5.33 (s, 2H), 7.03 (bd, J=8.5 Hz, 2H), 7.24 (bd, J=8.5 Hz, 2H), 7.85 (bd, J=8.5 Hz, 2H), 8.12 (bd, J=8.5 Hz, 2H), 11.7-12.4 (bm, 1H).

Example 32

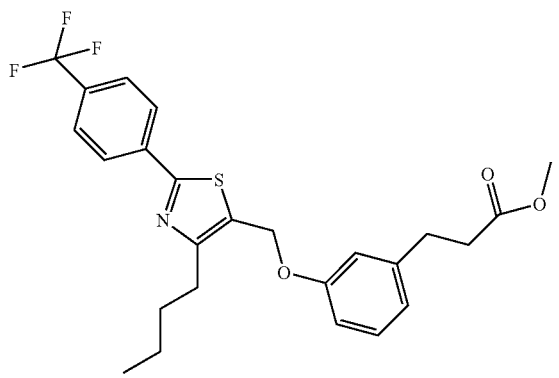

Intermediate: 3-{3-[4-Butyl-2-(4-trifluoromethyl-phenyl)-thiazol-5-ylmethoxy]-phenyl}-propionic acid methyl ester To a solution of 4-butyl-5-chloromethyl-2-(4-trifluoromethyl-phenyl)-thiazole (300 mg, 0.90 mmol) in anhydrous DMF (5 mL) add cesium carbonate (586 mg, 1.80 mmol) and methyl 3-(3-hydroxyphenyl)propionate (178 mg, 0.99 mmol). Stir the resulting mixture overnight then pour into water and extract twice with ethyl acetate. Wash the combined extracts with water, dry over MgSO$_4$, filter and concentrate under vacuum. Purify the residue by flash chromatography on silica gel (eluting with 5% ethyl acetate in heptane) to give the title compound (290 mg) as a yellow oil.

MS (ESI), m/z 478 (M+H); H1 NMR (DMSO-d6), δ 0.91 (t, J=7.5 Hz, 3H), 1.37 (m, 2H), 1.68 (m, 2H), 2.64 (m, 2H), 2.76-2.88 (m, 4H), 3.58 (s, 3H), 5.33 (s, 2H), 6.82-6.91 (m, 2H), 6.93 (bs, 1H), 7.22 (t, J=8.0 Hz, 1H), 7.85 (bd, J=8.5 Hz, 2H), 8.12 (bd, J=8.5 Hz, 2H).

Example 33

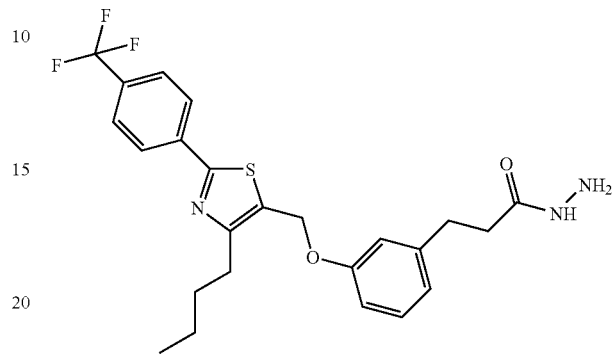

Intermediate: 3-{3-[4-Butyl-2-(4-trifluoromethyl-phenyl)-thiazol-5-ylmethoxy]-phenyl}-propionic acid hydrazide Follow the procedure of Example 8, but use the compound of Example 32 as the starting material to obtain the title compound.

MS (ESI), m/z 478 (M+H); H1 NMR (DMSO-d6), δ 0.91 (t, J=7.5 Hz, 3H), 1.36 (m, 2H), 1.68 (m, 2H), 2.33 (m, 2H), 2.80 (m, 4H), 4.14 (bd, J=4.0 Hz, 2H), 5.32 (s, 2H), 6.79-6.92 (m, 3H), 7.21 (t, J=7.5 Hz, 1H), 7.85 (bd, J=8.5 Hz, 2H), 8.12 (bd, J=8.5 Hz, 2H), 8.94 (bm, 1H).

Example 34

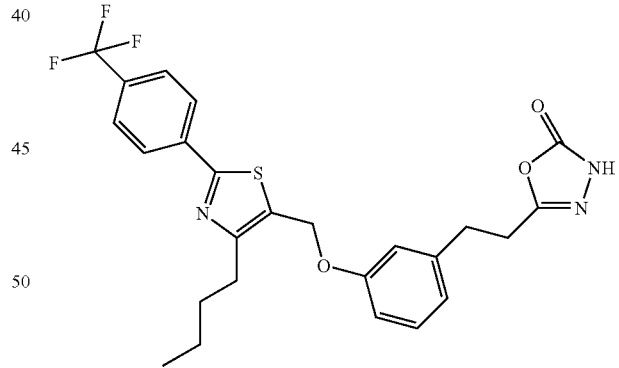

5-(2-{3-[4-Butyl-2-(4-trifluoromethyl-phenyl)-thiazol-5-ylmethoxy]-phenyl}-ethyl)-3H-[1,3,4]oxadiazol-2-one Follow the procedure of Example 10, but use the compound of Example 33 as the starting material to obtain the title compound.

MS (ESI), m/z 504 (M+H); H1 NMR (DMSO-d6), δ 0.91 (t, J=7.5 Hz, 3H), 1.36 (m, 2H), 1.67 (m, 2H), 2.80 (m, 2H), 2.88 (m, 4H), 5.33 (s, 2H), 6.83-6.93 (m, 2H), 6.97 (bs, 1H), 7.23 (t, J=8.0 Hz, 1H), 7.85 (bd, J=8.5 Hz, 2H), 8.12 (bd, J=8.5 Hz, 2H), 11.5-12.5 (bm, 1H).

What is claimed is:

1. A compound of formula I:

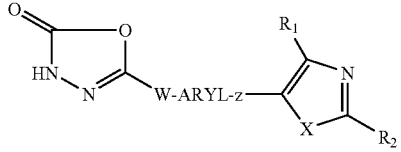

wherein
ARYL is phenyl or pyridinyl, wherein said phenyl or pyridinyl is optionally substituted with one or more substituents selected from the group consisting of halogen, $C_{1-6}$alkyl, $C_{2-6}$alkenyl, $C_{1-6}$alkoxy, $C_{1-6}$perfluoroalkyl, $C_{1-6}$alkylthio, hydroxy, hydroxy$C_{1-6}$alkyl, $C_{1-4}$acyloxy, nitro, cyano, $C_{1-6}$alkylsulfonyl, amino, $C_{1-6}$alkylamino and $C_{1-6}$alkoxycarbonyl;
W is a bond;
Z is —O(CH$_2$)$_n$—, —SO$_2$(CH$_2$)$_n$—, —(CH$_2$)$_n$—Y—(CH$_2$)$_n$—, —(CH$_2$)$_n$—CO—, —O(CH$_2$)$_n$—CO—, or —(CH$_2$)$_n$—Y—(CH$_2$)$_n$—CO— wherein Y is NR$_3$, O or S and R$_3$ is selected from the group consisting of H, $C_{1-6}$alkyl $C_{3-8}$cycloalkyl, $C_{1-6}$alkyl$C_{3-8}$cycloalkyl and benzyl and n is independently an integer from 1 to 5;
X is NR$_3$, O or S wherein R$_3$ is as defined above;
R$_1$ is H, halogen, $C_{1-6}$alkyl, $C_{1-6}$alkoxy, $C_{1-6}$perfluoroalkyl; hydroxy$C_{1-6}$alkyl, nitro, cyano, or $C_{1-6}$alkylamino; and
R$_2$ is substituted or unsubstituted phenyl, pyridinyl or thienyl wherein the substituents are selected from the group consisting of halogen, $C_{1-6}$alkyl, $C_{2-6}$alkenyl, $C_{1-4}$alkoxy, $C_{1-4}$perfluoroalkyl, $C_{1-6}$alkylthio, hydroxy, hydroxy$C_{1-6}$alkyl, $C_{1-4}$acyloxy, nitro, cyano, $C_{1-6}$alkylsulfonyl, amino, $C_{1-6}$alkylamino and $C_{1-6}$alkoxycarbonyl;
or a stereoisomer, or a tautomer thereof, or a pharmaceutically acceptable salt thereof.

2. The compound according to claim 1 wherein ARYL is phenyl or a stereoisomer, or a tautomer thereof, or a pharmaceutically acceptable salt thereof.

3. The compound according to claim 2 wherein ARYL is phenyl; and
R$_2$ is phenyl;
or a stereoisomer, or a tautomer thereof, or a pharmaceutically acceptable salt thereof.

4. The compound according to claim 3 wherein ARYL is phenyl;
Z is —O(CH$_2$)$_n$—; and
R$_2$ is phenyl;
or a stereoisomer, or a tautomer thereof, or a pharmaceutically acceptable salt thereof.

5. The compound according to claim 4 wherein ARYL is phenyl;
Z is —O(CH$_2$)$_n$—;
X is O or S; and
R$_2$ is phenyl;
or a stereoisomer, or a tautomer thereof, or a pharmaceutically acceptable salt thereof.

6. The compound according to claim 5 wherein ARYL is phenyl;
Z is —O(CH$_2$)$_n$—;
X is O or S;
R$_1$ is $C_{1-6}$alkyl; and
R$_2$ is phenyl;
or a stereoisomer, or a tautomer thereof, or a pharmaceutically acceptable salt thereof.

7. The compound according to claim 6 wherein X is O;
or a stereoisomer, or a tautomer thereof, or a pharmaceutically acceptable salt thereof.

8. The compound according to claim 6 wherein X is S;
or a stereoisomer, or a tautomer thereof, or a pharmaceutically acceptable salt thereof.

9. The compound according to claim 8 wherein ARYL is phenyl;
Z is —(CH$_2$)$_n$—Y—(CH$_2$)$_n$—; and
R$_2$ is phenyl;
or a stereoisomer, or a tautomer thereof, or a pharmaceutically acceptable salt thereof.

10. The compound according to claim 9 wherein ARYL is phenyl;
Z is —(CH$_2$)$_n$—Y—(CH$_2$)$_n$—;
X is O or S; and
R$_2$ is phenyl;
or a stereoisomer, or a tautomer thereof, or a pharmaceutically acceptable salt thereof.

11. The compound according to claim 10 wherein ARYL is phenyl;
Z is —(CH$_2$)$_n$—Y—(CH$_2$)$_n$—;
X is O or S; and
R$_1$ is $C_{1-6}$alkyl; and
R$_2$ is phenyl;
or a stereoisomer, or a tautomer thereof, or a pharmaceutically acceptable salt thereof.

12. The compound according to claim 11 wherein X is S;
or a stereoisomer, or a tautomer thereof, or a pharmaceutically acceptable salt thereof.

13. The compound of claim 11 wherein X is O;
or a stereoisomer, or a tautomer thereof, or a pharmaceutically acceptable salt thereof.

14. The compound according to claim 1, which is selected from the group consisting of:
5-{4-[4-methyl-2-(4-trifluoromethyl-phenyl)-thiazol-5-ylmethoxy]-phenyl}-3H-[1,3,4]oxadiazol-2-one,
5-[4-(4-methyl-2-m-tolyl-oxazol-5-ylmethoxy)-phenyl]-3H-[1,3,4]oxadiazol-2-one,
5-{4-[4-methyl-2-(4-trifluoromethyl-phenyl)-thiazol-5-yl)-methoxymethyl]-phenyl}-3H-[1,3,4]oxadiazol-2-one,
5-{3-[4-methyl-2-(4-trifluoromethyl-phenyl)-thiazol-5-yl)-methoxymethyl]-phenyl}-3H-[1,3,4]oxadiazol-2-one,
5-{4-[4-butyl-2-(4-trifluoromethyl-phenyl)-thiazol-5-ylmethoxy]-2-chloro-phenyl}-3H-[1,3,4]oxadiazol-2-one,
5-{4-[4-butyl-2-(4-trifluoromethyl-phenyl)-thiazol-5-ylmethoxymethyl]-2-fluoro-phenyl}-3H-[1,3,4]oxadiazol-2-one,
5-{4-[4-butyl-2-(4-trifluoromethyl-phenyl)-thiazol-5-ylmethoxy]-benzyl }-3H-[1,3,4]oxadiazol-2-one, and
5-(2-{3-[4-butyl-2-(4-trifluoromethyl-phenyl)-thiazol-5-ylmethoxy]-phenyl}-ethyl)-3H-[1,3,4]oxadiazol-2-one;
or a stereoisomer, or a tautomer thereof, or a pharmaceutically acceptable salt thereof.

15. A pharmaceutical composition comprising an effective amount of the compound according to claim 1, or a stereoisomer, or a tautomer thereof, or a pharmaceutically acceptable salt thereof, and a pharmaceutically acceptable carrier.

* * * * *